United States Patent [19]
Xiao et al.

[11] Patent Number: 6,013,515
[45] Date of Patent: Jan. 11, 2000

[54] COFACTORS FOR HIV-1 PROTEIN TAT AND METHODS OF USE THEREFOR

[75] Inventors: Hua Xiao, New York, N.Y.; Jack Fred Greenblatt, Toronto, Canada; Robert G. Roeder, New York, N.Y.

[73] Assignee: The Rockefeller University, New York, N.Y.

[21] Appl. No.: 08/908,332

[22] Filed: Aug. 7, 1997

[51] Int. Cl.[7] .............................. C12N 15/63; C12N 1/21; C12N 5/10; C07H 21/04

[52] U.S. Cl. ...................................... 435/320.1; 435/252.3; 435/252.33; 435/325; 435/348; 435/354; 435/366; 536/23.5

[58] Field of Search ...................................... 435/455, 456, 435/468, 471, 472, 325, 348, 354, 366, 410, 252.3, 252.31–252.35, 320; 536/23.5

[56] References Cited

PUBLICATIONS

Cuject et al(1997) Mol Cell Biol 17:1817–23.
Cuject et al (1997) Genes & Develop. 11:2645–57.
Cullen(1994) Infect Agent Dis 3:68–76.
Emili et al(1994) Mol Cell Biol 14:1582–93.
Feng et al(1988) Nature 334:165–7.
Fridell et al(1995) Virology 209:347–57.
Garcia et al(1989) EMBO J 8:765–78.
Gross et al(1990) J Biol Chem 265:6896–907.
Jones, K.A. (1997) Genes & Develop. 11:2593–9.
Jones et al(1994) Annu Rev Biochem 63:717–43.
Kamine et al(1996) Virology 216:357–66.
Karn et al(1992) Trends Genet 8:365–8.
Mancebo et al. (1997) Genes & Develop. 11:2633–44.
Nelbock et al(1990) Science 248:1650–3.
Parada et al(1986) Nature 384:375–8.
Rosen et al(1985) Cell 41:81323.
Selby et al(1989) Genes Dev 3:547–58.
Shibuya et al(1992) Nature 357:700–2.
Shtivelman, E. (1997) Oncogene 14:2167–73.
Southgate et al(1991) Genes Dev 5:2496–507.
Sune et al(1995) J Virol 69:3098–107.
Wu et al(1991) Genes and Dev 5:2128–40.
Wu–Baer et al(1996) J Biol chem 271:4201–5.
Yu et al(1995) J Virol 69:3007–16.
Zhou et al(1996) Science 274:605–10.
Zhou et al(1995) EMBO J 14:321–8.
Zhu et al. (1997) Genes & Develop. 11:2622–32.
Xiao et al., *Proc. Natl. Acad. Sci. USA* 95:2146–2151, Mar. 1998.

*Primary Examiner*—Robert D. Budens
*Attorney, Agent, or Firm*—Klauber & Jackson

[57] ABSTRACT

Methods of isolating and characterizing Tat-interacting proteins (TIPs) are disclosed. These Tat-interacting proteins comprise a material selected from the group consisting of a protein, active fragments thereof, agonists thereof, mimics thereof, and combinations thereof, said protein having the following characteristics:

a) it binds with the activation domain of the HIV-1 regulatory protein Tat and stimulates transactivation by Tat and b) it possesses an apparent molecular weight of approximately 30 kDa or 56 kDa as determined by SDS-polyacrylamide gel electrophoresis.

17 Claims, 12 Drawing Sheets

FIG. 2A

MAETEALSKLREDFRMQNKSVFILGASGETGRVLLKEILEQGLFSKVTLI
GRRKLTFDEEAYKNVNQEVVDFEKLDDYASAFQGHDVGFCCLGTTRGK
AGAEGFVRVDRDYVLKSAELAKAGGCKHFNLLSSKGADKSSNFLYLQV
KGEVEAKVEELKFDRYSVFRPGVLLCDRQESRPGERLVRKFFGSLPDSW
ASGHSVPVVTVVRAMLNNVVRPRDKQMELLENKAIHDLGKAHGSLKP*

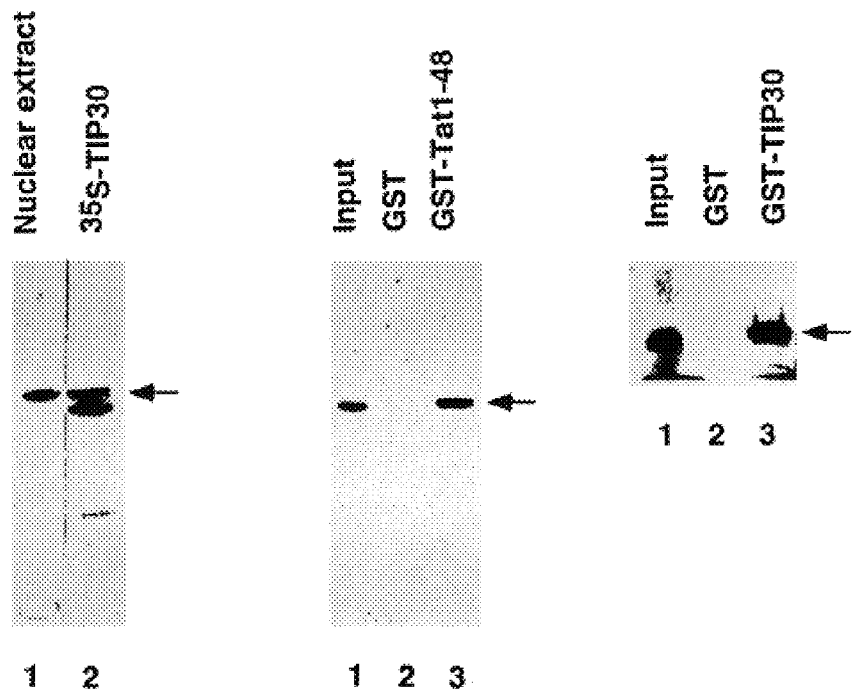

Mouse TIP 1
MADKEALRKLREDFKMQNKSVFILGASGETGKVLLKEIVGQNLFSKVT
LIGRRKLTFEEEAYKNVNQEVVDFEKLDVYASAFQGHDVGFCCLGTTR
SKAGAEGFVRVDRDYVLKSAELAKAGGCKHFNLLSSRGADKSSSFLYL
QVKGEVEAKVEELKFDRLSVFRPGVLLCDRQESRPGEWLARKFFGSLP
DSWASGYAVPVVTVVRAMLNSLVSPSSGQMELLENKAILHLGKDRDVP
KL*

FIG. 5A

```
                        10         20         30         40         50         60
Ecoli       
Yeast                                                    MSRGAQGRQFCKGAKMSQVLITGATGLVGGHLIRMLINEPKVNAIAAPTRR---PLG--
C.elegans                   MNGLVLGATGLCGGGFLRHAQEAPQFSKVYAILRRELPFPAT
Human                           MSSAFVVGATGAVGSEIVKLLAESTKFSKVVLARR--PVDGA
            MAETEALSKLREDFRMQNKSVFLGASGETGRVLLKEILEQGLFSKVTLIGRRKLTFDEE 70         80         90        100        110        120
Ecoli       DMPGVFNP-HDPQLSDAIAQVTDPIDIVFCCLGTTRREAGSKEAFIHADYTIVDTALTG
Yeast       DKVAIVE-RDNSKWSQLITNEMNPQVLFTALATTRAAAGGLDKQYKIDHDLNLQLAQAA
C.elegans   TGDKLIQKTVDFDKLEENAEDIQGVDVAFCALGTTRGKSG-ADGFYKVDHDYVMSAAKMA
Human       AYKNVNQEVVDFEKLDDYASAFQGHDVGFCCLGTTRGKAG-AEGFVRDRDYVLKSAELA 130        140        150        160        170        180
Ecoli       RRLGAQHMLVVSAMGANAHSPFFYNRVKGEMEEALIAQNWPKLTTARPSMILGDRSKQRM
Yeast       KEKGCETIVILVSSAGAAHPDSRFGYMKGEIERDVIALDFKHIIIIRPGPLLGERTNSKQ
C.elegans   KENGVKQFVLVSSVGADASSRFLIYPKTKGEVEKEIGELNFEKFVIMRPGLIEAKPEFRI
Human       KAGGCKHFNLISSKGADKSSNFHYLQVKGEVEAKVEELKFDRYSVFRPGVILCDRQESRP 190        200        210        220        230        240
Ecoli       ----NETLFAPLFRIIP--GN-WKSIDARDVARVMLAESMRPEHEG---VTILSSELRK
Yeast       SGFGGNLTAALGTRVYRSRFQRLLGYPVYGDEVGKVGVHLALNTSGKDKVQFVSSKDILD
C.elegans   ----GEFIGKIVTAPIG-LFSNRFSSSATAIAQAMIN-ATQTEETG---NQIWNNSKIVE
Human       ----GERLVRKFFGSIPDSWASGHSVPVVTVVRAMLNNVVRPRDKQ---MELLENKAIHD 250
Ecoli       RAE
Yeast       ISASLEKIAT
C.elegans   ESKKYTA
Human       LGKAHGSLKP
```

FIG. 5B

```
 23 SLKEFLDKAREDFKQRWENPAQNTACLDDFDRIKTLGTGSFGRVMLVKHK  72
    . .| |.| ||||:          ::: . :     :.|. |||:| .
  2 AETEALSKLREDFR...........MQNKSVFILGASGETGRVLLKEIL  39

73 QSGNYYAMKILDKQKVVKLKQVEHTLNEKRILQAIDFPFLVNMTFSLKDN 122
    : | :  :.:::::.|:.  .:.  ..:|:     :.:||. | : .::::
 40 EQGLFSKVTLIGRRKLTFDEEAYKNVNQ....EVVDFEKLDDYASAFQGH  85

123 SNLYMVLEFISGGEMFSHLRRIGR.FSEPHSRFYAAQIVLAFEYLHSLDL 171
    . : .|: ..| .  . : |::| :  . .  |.. |:.| | :
 86 DVGFCCLGTTRGKAGAEGFVRVDRDYVLKSAELAKAGGCKHFNLLSSKG. 134

172 IYRDLKPENLLIDSTGYLKVTDFGFAKRVKGRTWTLCGTPEYLAPEIILS 221
      . |..|:|     ||.|.: :.. :|.: .:. ::.    : |:::|:
135 ...ADKSSNFL.....YLQVKG.EVEAKVEELKFDRYSV...FRPGVLLC 172

222 KGYNKAVDWWALGVLIYEMAAGYPPFFADQPIQIYEKIVSGKVKFPSHFS 271
      :.:: : |: .: ::.|. :|...    .:|.:.: . .
173 ....DRQESRPGERLVRKFFGSLPDSWASGHSVPVVTVVRAMLNNVVRPR 218

272 NELKDLLKNLLQVDLTKRYGNLK 294
    :.. .:||.|    ||.| .|.||
219 DKQMELLENKAIHDLGKAHGSLK 241
```

| | | | | |
|---|---|---|---|---|
| pSVL | + | − | − | + |
| pSVTat | − | + | + | − |
| pcDNA3.1 | + | + | − | − |
| pcDNA3.1TIP30 | − | − | + | + |

1  2  3  4

| | | | | | | | | |
|---|---|---|---|---|---|---|---|---|
| pSVL | + | − | − | − | − | − | − | + |
| pGalVP16 | − | + | − | − | + | − | − | − |
| pGalp53 | − | − | + | − | − | + | − | − |
| pGalE1A | − | − | − | + | − | − | + | − |
| pcDNA3.1 | + | + | + | + | − | − | − | − |
| pcDNA3.1TIP30 | − | − | − | − | + | + | + | + |

```
          10         20         30         40         50         60
GTCTGGCCAGACATGGCCGAAACAGAAGCCCTGTCGAAGCTTCGGGAAGACTTCAGGATG
CAGACCGGTCTGTACCGGCTTTGTCTTCGGGACAGCTTCGAAGCCCTTCTGAAGTCCTAC 70         80         90        100        110        120
CAGAATAAATCCGTCTTTATTTTGGGCGCCAGCGGAGAAACCGGCAGAGTGCTCTTAAAG
GTCTTATTTAGGCAGAAATAAAACCCGCGGTCGCCTCTTTGGCCGTCTCACGAGAATTTC 130        140        150        160        170        180
GAAATCCTGGAGCAGGGCCTGTTTTCCAAAGTCACGCTCATTGGCCGGAGGAAGCTCACC
CTTTAGGACCTCGTCCCGGACAAAAGGTTTCAGTGCGAGTAACCGGCCTCCTTCGAGTGG 190        200        210        220        230        240
TTCGACGAGGAAGCTTATAAAAATGTGAATCAAGAAGTGGTGGACTTTGAAAAGTTGGAT
AAGCTGCTCCTTCGAATATTTTTACACTTAGTTCTTCACCACCTGAAACTTTTCAACCTA 250        260        270        280        290        300
GACTACGCCTCTGCCTTTCAAGGTCATGATGTAGGATTCTGTTGCCTGGGTACCACCAGA
CTGATGCGGAGACGGAAAGTTCCAGTACTACATCCTAAGACAACGGACCCATGGTGGTCT 310        320        330        340        350        360
GGGAAAGCTGGGGCGGAGGGATTTGTTCGTGTTGACCGAGATTATGTGCTGAAGTCTGCA
CCCTTTCGACCCCGCCTCCCTAAACAAGCACAACTGGCTCTAATACACGACTTCAGACGT 370        380        390        400        410        420
GAGCTGGCAAAAGCTGGAGGGTGCAAACATTTCAACTTGCTATCCTCTAAAGGAGCTGAT
CTCGACCGTTTTCGACCTCCCACGTTTGTAAAGTTGAACGATAGGAGATTTCCTCGACTA 430        440        450        460        470        480
AAATCAAGCAATTTTTTATATCTACAAGTTAAGGGAGAAGTAGAAGCCAAGGTTGAAGAA
TTTAGTTCGTTAAAAAATATAGATGTTCAATTCCCTCTTCATCTTCGGTTCCAACTTCTT 490        500        510        520        530        540
TTAAAATTTGATCGTTACTCTGTATTTAGGCCTGGAGTTCTGTTATGTGATAGGCAAGAA
AATTTTAAACTAGCAATGAGACATAAATCCGGACCTCAAGACAATACACTATCCGTTCTT 550        560        570        580        590        600
TCTCGCCCAGGTGAACGGCTGGTTAGAAAGTTCTTTGGCTCCTTACCAGACTCTTGGGCC
AGAGCGGGTCCACTTGCCGACCAATCTTTCAAGAAACCGAGGAATGGTCTGAGAACCCGG 610        620        630        640        650        660
AGTGGGCATTCTGTGCCTGTGGTGACCGTGGTTAGAGCAATGCTGAACAATGTGGTGAGA
TCACCCGTAAGACACGGACACCACTGGCACCAATCTCGTTACGACTTGTTACACCACTCT 670        680        690        700        710        720
CCAAGAGACAAGCAGATGGAACTGCTGGAGAACAAGGCCATCCATGACCTGGGGAAAGCG
GGTTCTCTGTTCGTCTACCTTGACGACCTCTTGTTCCGGTAGGTACTGGACCCCTTTCGC 730        740        750        760        770        780
CATGGCTCTCTCAAGCCATGACCACATTGGAGAAATGGTTTTTATTGTCAACCTTAACAC
GTACCGAGAGAGTTCGGTACTGGTGTAACCTCTTTACCAAAAATAACAGTTGGAATTGTG 790        800        810        820        830        840
CCATCACCAAATCGGTAATTTCAGGGTCTAAAAAAGTCAGCATGTTTTAACTTTGTTGT
GGTAGTGGTTTAGCCATTAAAGTCCCAGATTTTTTCAGTCGTACAAAATTGAAACAACA 850        860        870        880        890        900
```

FIG. 8A - 2

```
TTTACTATCCTCAGGATCCATTCCAATCAAGAAATGATGGCTCTGGGTCAGTGGTTCAGA
AAATGATAGGAGTCCTAGGTAAGGTTAGTTCTTTACTACCGAGACCCAGTCACCAAGTCT 910       920       930       940       950       960
GCCTGGTTATACATATAGATCACTCAGGGAGCTTCCCCCAAATAAAGATTTGTCACCCTA
CGGACCAATATGTATATCTAGTGAGTCCCTCGAAGGGGGTTTATTTCTAAACAGTGGGAT 970       980       990      1000      1010      1020
TCTCAAACAAGAATCAAAATTTCTGGGGCACAATAATCTGTAATTTTCTTGTTTATACTT
AGAGTTTGTTCTTAGTTTTAAAGACCCCGTGTTATTAGACATTAAAAGAACAAATATGAA 1030      1040      1050      1060      1070      1080
CCCCTGATGCCACTGGTTCCGATGCACTGGCTGGGGGGCCTGCTTTGAAATGCTTGTCTG
GGGGACTACGGTGACCAAGGCTACGTGACCGACCCCCGGACGAAACTTTACGAACAGAC 1090      1100      1110      1120      1130      1140
CAGAGTCACAGCAGCCATGAAAACCTTATGACCGTGCAAATGATCTGCTCTAAAATTGTT
GTCTCAGTGTCGTCGGTACTTTTGGAATACTGGCACGTTACTAGACGAGATTTTAACAA 1150      1160      1170      1180      1190      1200
GACATTCATGTCTCTGAGTTACAAAAGTGCTAATTCACTACATGTAATTGTGTAAGTAAA
CTGTAAGTACAGAGACTCAATGTTTTCACGATTAAGTGATGTACATTAACACATTCATTT 1210      1220      1230      1240      1250      1260
CATTGTGCCTTTACTACTTCTTTATGTAATAGAAGTTATATCCTAAGCTTATATAATACA
GTAACACGGAAATGATGAAGAAATACATTATCTTCAATATAGGATTCGAATATATTATGT 1270      1280      1290      1300      1310
TGGGGAGGATTAAATAAAGGAATAAAGATGAATGGACAAAAAAAAAAAAAAAAA
ACCCCTCCTAATTTATTTCCTTATTTCTACTTACCTGTTTTTTTTTTTTTTTT
```

FIG. 8B-1

```
          10         20         30         40         50         60
AAGCAGGACCATGATACCCCAAGTTGGAAATTAACCCTTCATTAAAGGGAACAAAAAGTT
TTCGTCCTGGTACTATGGGGTTCAACCTTTAATTGGGAAGTAATTTCCCTTGTTTTTCAA 70         80         90        100        110        120
GGTACCGGCCCCCCCTCGAGCGCCGCCGGGCAGGTGATTTTTTTTGCCCAACATTAACA
CCATGGCCGGGGGGGAGCTCGCGGCGGCCCGTCCACTAAAAAAAACGGGTTGTAATTGT 130        140        150        160        170        180
ACCCTTTCCCCCAGGGTAAAGAGTGTCACTAGCATTTTGAGACAGGACCCACGGGTGTTG
TGGGAAAGGGGGTCCCATTTCTCACAGTGATCGTAAAACTCTGTCCTGGGTGCCCACAAC 190        200        210        220        230        240
TTTCCCCCAGCATGGCGGACAAGGAAGCACTGCGGAAGCTTCGGGAAGATTTCAAGATGC
AAAGGGGGTCGTACCGCCTGTTCCTTCGTGACGCCTTCGAAGCCCTTCTAAAGTTCTACG 250        260        270        280        290        300
AGAATAAATCCGTCTTTATTTTGGGCGCCAGCGGGGAAACTGGCAAAGTACTTTTAAAGG
TCTTATTTAGGCAGAAATAAAACCCGCGGTCGCCCCTTTGACCGTTTCATGAAAATTTCC 310        320        330        340        350        360
AAATCGTGGGACAGAACCTGTTTTCCAAAGTAACGCTCATTGGTCGGAGGAAGCTCACCT
TTTAGCACCCTGTCTTGGACAAAAGGTTTCATTGCGAGTAACCAGCCTCCTTCGAGTGGA 370        380        390        400        410        420
TCGAGGAGGAAGCTTATAAAAATGTGAATCAAGAAGTGGTGGACTTTGAGAAGCTGGATG
AGCTCCTCCTTCGAATATTTTTACACTTAGTTCTTCACCACCTGAAACTCTTCGACCTAC 430        440        450        460        470        480
TCTATGCTTCTGCCTTTCAAGGTCATGATGTTGGATTCTGTTGCCTGGGCACCACCAGAA
AGATACGAAGACGGAAAGTTCCAGTACTACAACCTAAGACAACGGACCCGTGGTGGTCTT 490        500        510        520        530        540
GCAAGGCTGGAGCGGAAGGGTTTGTTCGTGTTGACCGAGATTATGTGCTCAAGTCTGCAG
CGTTCCGACCTCGCCTTCCCAAACAAGCACAACTGGCTCTAATACACGAGTTCAGACGTC 550        560        570        580        590        600
AGCTGGCGAAAGCAGGAGGGTGCAAACATTTCAACTTGCTGTCCTCCAGGGGGGCCGATA
TCGACCGCTTTCGTCCTCCCACGTTTGTAAAGTTGAACGACAGGAGGTCCCCCCGGCTAT 610        620        630        640        650        660
AGTCCAGCAGTTTCTTATACCTACAAGTAAAGGGAGAAGTGGAAGCCAAGGTTGAAGAAT
TCAGGTCGTCAAAGAATATGGATGTTCATTTCCCTCTTCACCTTCGGTTCCAACTTCTTA 670        680        690        700        710        720
TAAAGTTTGATCGACTCTCAGTGTTTCGGCCAGGAGTCCTACTGTGTGACAGGCAAGAGT
ATTTCAAACTAGCTGAGAGTCACAAAGCCGGTCCTCAGGATGACACACTGTCCGTTCTCA 730        740        750        760        770        780
CTCGTCCAGGCGAATGGCTGGCTAGGAAATTCTTCGGCTCTCTGCCAGACTCTTGGGCCA
GAGCAGGTCCGCTTACCGACCGATCCTTTAAGAAGCCGAGAGACGGTCTGAGAACCCGGT 790        800        810        820        830        840
GTGGGTACGCTGTGCCTGTGGTGACGGTGGTTAGAGCGATGCTGAACAGCCTGGTGAGTC
CACCCATGCGACACGGACACCACTGCCACCAATCTCGCTACGACTTGTCGGACCACTCAG 850        860        870        880        890        900
```

FIG. 8B - 2

```
CCAGCAGCGGACAAATGGAACTTCTGGAAAATAAGGCCATCCTCCACCTGGGGAAAGACA
GGTCGTCGCCTGTTTACCTTGAAGACCTTTTATTCCGGTAGGAGGTGGACCCCTTTCTGT 910       920       930       940       950       960
GGGATGTGCCCAAACTGTGACCATGCTGGAGGACATTCGTGAAACCTCAGTGCCTGTCA
CCCTACACGGGTTTGACACTGGTACGACCTCCTGTAAGCACTTTTGGAGTCACGGACAGT 970       980       990      1000      1010      1020
CCAAATCAGTCATTTGGGGGCTCTATAAAAGTCTCTTTGTGGTCCTTTGTGGTGTGCTT
GGTTTAGTCAGTAAACCCCGAGATATTTTCAGAGAAACACCAGGAAACACCACACGAA 1030      1040      1050      1060      1070      1080
CTCCTTAGCCAAGCGGCTCCATCAGAAAATGGCACTACTCCACGTCAGTTGTTGAGAGCC
GAGGAATCGGTTCGCCGAGGTAGTCTTTTACCGTGATGAGGTGCAGTCAACAACTCTCGG 1090      1100      1110      1120      1130      1140
CCGTTGCTCATGTAATCATCCAGGCAGCTTTTGGAGAACAGGTTTATATCATAGACTTAT
GGCAACGAGTACATTAGTAGGTCCGTCGAAAACCTCTTGTCCAAATATAGTATCTGAATA 1150      1160      1170
ACTTTGTAGGTTGCAAACAGGGATCTCTGGAGGTCACG
TGAAACATCCAACGTTTGTCCCTAGAGACCTCCAGTGC
```

COFACTORS FOR HIV-1 PROTEIN TAT AND METHODS OF USE THEREFOR

This invention was supported by partial assistance from Grant No. A137327 from the National Institutes of Health/Tebil Foundation. The government may have certain rights in the invention.

TECHNICAL FIELD OF THE INVENTION

The present invention relates generally to cofactors which interact with the activation domain of Tat which increase the rate of transcription from the viral long terminal repeat (LTR) during viral growth of the human immunodeficiency virus 1 (HIV-1).

BACKGROUND OF THE INVENTION

The human immunodeficiency virus (HIV-1), the etiologic agent of acquired immunodeficiency syndrome (AIDS), encodes a number of regulatory proteins. One of them, called Tat, is required primarily to increase the rate of transcription from the viral long terminal repeat (LTR) during viral growth and may also regulate expression of cellular genes and mediate apoptosis. Tat can be taken up by HeLa cells and localizes rapidly to the nucleus.

Despite extensive study, the mechanism of Tat-responsive action is still poorly understood. In most cellular assay systems and the cell free systems, the major effects of Tat are on transcription elongation, but effects on the rate of initiation have also been reported. Transactivation by Tat is critically dependent upon upstream Sp1 binding sites in the DNA and on an RNA sequence, called TAR, which is encoded by DNA sequences downstream of the site of transcription initiation. The Sp1-binding sites interact with the cellular transactivator Sp1 that cooperates with Tat, bound to TAR, to stimulate transcription. Tat can also function when bound to DNA as a GAL4 fusion protein. Genetic and biochemical studies have suggested that a human-specific factor acts as a Tat cofactor to facilitate binding of Tat to TAR and mediates transcriptional activation. This putative cofactor is probably encoded by a gene on human chromosome 12 because human chromosome 12 greatly stimulates Tat-responsive activation in rodent cells. Furthermore, high levels of the amino-terminal portion of Tat can squelch transactivation by Tat and chimeric Tat proteins in vivo and in vitro, suggesting that at least one coactivator may interact with the amino-terminal portion of Tat. A partially purified cofactor can support Tat-activated transcription in an in vitro transcription system containing Sp1, highly purified general transcription factors and RNA polymerase II. Several candidate coactivators, including TBP1 (Nelbock et al., 1990, *Science* 248:1650) have been identified. Although these proteins have some of the expected characteristics of a coactivator, none has been determined to interact directly with the amino-terminal portion of Tat and to participate directly in the action of Tat as a cofactor. A cellular acidic activator, Tat-associated protein (TAP) has been shown to interact directly with the core domain of Tat and the general transcription factor TFIIB (Yu et al., 1995, *J. Virol.* 69:3007). However, since TAP is conserved among eukaryotes and is expressed in human and rodent cells, it can be excluded as a species-specific cofactor for Tat.

In order to develop effective therapies for the treatment and prevention of AIDS, elucidation of the mechanisms by which it replicates in the human host is essential. Therefore, in view of the aforementioned deficiencies attendant to this mechanism, it is apparent that there still exists a need in the art for the identification and characterization of the cofactors which participate in the HIV-1 transcription process.

SUMMARY OF THE INVENTION

In accordance with the present invention, there is provided Tat-interacting proteins (TIPs), and methods of use therefor. In a further embodiment, methods of isolating and characterizing a novel Tat-interacting protein 30 (TIP30) of the present invention are disclosed. In its broadest aspect, the present invention extends to a Tat-interacting proteins which comprise a material selected from the group consisting of a protein, active fragments thereof, agonists thereof, mimics thereof, and combinations thereof, said protein having the following characteristics:

a) it binds with the activation domain of the HIV-1 regulatory protein Tat and stimulates transactivation by Tat; and b) it possesses an apparent molecular weight of approximately 30 kDa or 56 kDa as determined by SDS-polyacrylamide gel electrophoresis.

Accordingly, it is a principal object of the present invention to provide a novel Tat-interacting protein 30 (TIP30), which possesses an apparent molecular weight of approximately 30 kDa as determined by SDS-polyacrylamide gel electrophoresis, and its subunits in purified form that exhibits certain characteristics and activities associated with the interaction of the Tat-interacting protein (TIP) with the Tat regulatory protein and their combined transcriptional activity.

It is also an object of the present invention to provide antibodies to the Tat-interacting protein 30 (TIP30) and its subunits, and methods for their preparation, including recombinant means.

It is a further object of the present invention to provide a method for detecting the presence of the Tat-interacting proteins (TIPs) and its subunits in mammals in which invasive, spontaneous, or idiopathic pathological states are suspected to be present.

It is a yet another object of the present invention to provide a method and associated assay system for screening substances such as drugs, agents and the like, potentially effective in combating the adverse effects of the Tat-interacting proteins (TIPs) and/or its subunits in mammals.

It is a still further object of the present invention to provide a method for the treatment of mammals to control the amount or activity of the Tat-interacting proteins (TIPs) or subunits thereof, so as to alter the adverse consequences of such presence or activity.

It is an object of the present invention to provide a method for the treatment of mammals to control the amount or activity of the Tat-interacting proteins (TIPs) or subunits thereof, so as to treat or avert the adverse consequences of invasive, spontaneous or idiopathic pathological states resultant from HIV-1 infection.

It is a still further object of the present invention to provide pharmaceutical compositions for use in therapeutic methods which comprise or are based upon the Tat-interacting protein 30 (TIP30), its subunits, their binding partner(s), or upon agents or drugs that control the production, or that antagonize the activities of the Tat-interacting protein 30 (TIP30).

Other objects and advantages will become apparent to those skilled in the art from a review of the ensuing description which proceeds with reference to the following illustrative drawings.

BRIEF DESCRIPTION OF THE DRAWINGS

FIG. 1 depicts a photograph of a gel showing that the activation domain of Tat binds to a 30 kDa protein and a 56 kDa protein. Aliquots of HeLa whole cell extract were chromatographed on affinity columns containing GST and GST-Tat (1–48) by Blau et al., *Mol. Cell. Biol.* 16, 2044 (1996) and Xiao et al., *Mol. Cell. Biol.* 16, 7013 (1994). Bound proteins were subjected to SDS-PAGE on a 10% gel and stained with silver. Arrows indicate the 30 kDa and 56 kDa proteins.

FIG. 2A shows the deduced amino acid sequence of human TIP1 (SEQ ID NO:1).

FIG. 2B shows that the cDNA encodes a full length TIP1. Recombinant TIP1 was expressed as described below in Example 2.2 μl of HeLa nuclear extract (lane 1) and 1 μl of in vitro translation mixture containing $^{35}$S-methionine labeled recombinant TIP1 (lane 2) were resolved by SDS-PAGE (10%) and transferred onto a nitrocellulose membrane. The endogenous TIP1 was visualized by immunoblotting with antibodies raised against bacterially expressed TIP1 and recombinant TIP1 was visualized by autoradiography.

FIG. 2C shows that anti-TIP1 antibody recognizes a 30 kDa nuclear extract protein that binds to the activation domain of Tat. 200 μl of HeLa nuclear extract was chromatographed on 40 μl GST and GST-Tat (1–48) colurnns. The columns were washed with BC buffer (20 mM Tris-HCI, pH 7.9, 0.2 mM EDTA, 1 mMDTT and 20% glycerol) containing 100 mM KCI (BC100) and eluted with 160 μl of BC1000 buffer. Proteins eluted form the columns were separated on SDS-PAGE and immunoblotted with anti-TIP1 antibody Lane 1, 10% of the input HeLa nuclear extract. Lane 2, 25% of the GST column eluate. Lane 3, 25% of the GST-Tat column eluate.

FIG. 2D shows the binding of Tat to the GST-TIP1. The binding assay was performed as described in Example below. Lane 1, 10% of the input containing $35_S$-methionine labeled Tat (1–72) made in a reticulocyte lysate translation/transcription system. Lane 2, 25% of the eluate from the GST beads. Lane 3, 25% of the eluate from the GST-TIP1 beads.

FIG. 2E shows the amino acid sequence of mouse TIP 1 (SEQ ID NO:2).

Figure 3:
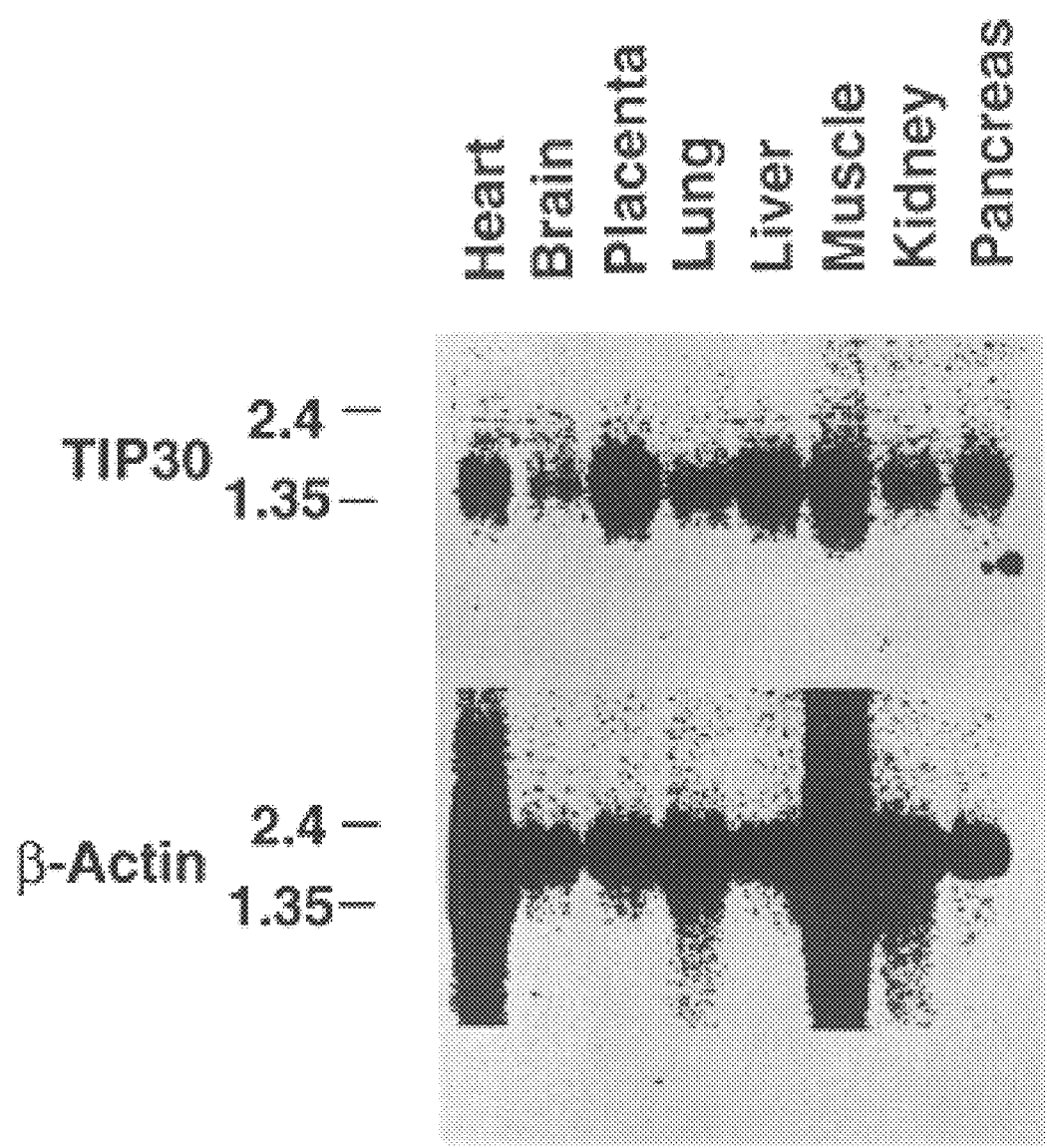

FIG. 3 shows a Northern blot analysis of TIP1 mRNA. A Northern blot (Clontech) containing 2 μg of poly A+RNA from each of the human tissues indicated at the top was hybridized to a labeled DNA fragment containing the entire open reading frame of TIP1 (top) and a β-actin DNA probe (bottom). The probes were labeled with a random primed DNA labeling kit (Boehringer Mannheim). Northern analyses were performed as instructed by the manufacturer (Clontech). The bands were quantified by phosphorimager (Molecular dynamic storm 840).

Figure 4A:
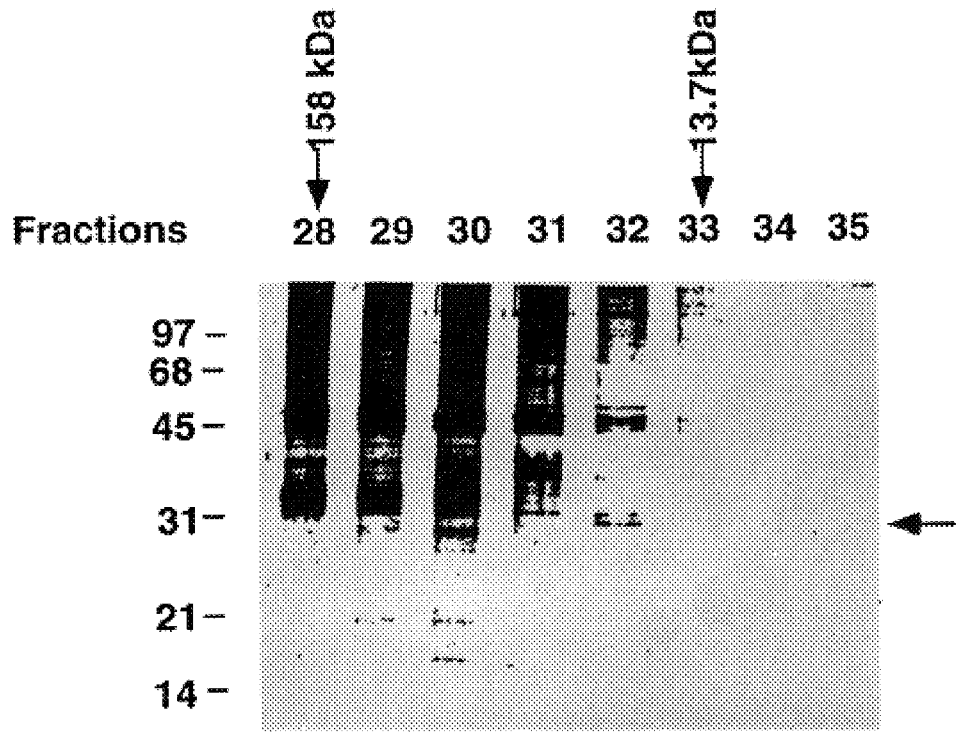
Figure 4B:
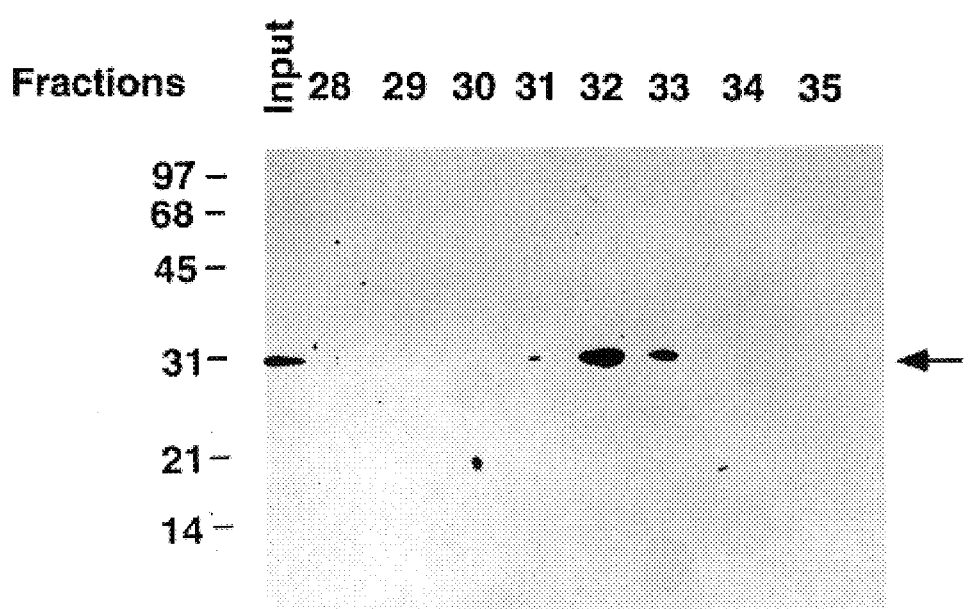

FIG. 4 indicates that TIP1 has a native size of about 25 kDa. HeLa nuclear extract (10 mL) was chromatographed on a GST-Tat (1–48) affinity column (0.5 mL) in BC100 buffer. Bound proteins were eluted with 2 ml of BC1000 buffer and then applied to a Sephacryl S-400 column (Pharmacia) and washed with BC100 containing 0.02% NP40 (100 mL) and aliquots were subjected to SDS-PAGE followed by silver staining (top panel) and immunoblotting with anti-TIP1 antibody (bottom panel. The arrowheads indicate TIP1.

FIG. 5A is an amino acid sequence comparison among TIP1, *E. coli* ORF-f226, yeast YEJ4 and a Caenorhabditis elegans hypothetical protein. Comparisons were made by MacVector 6.0. Similar amino acids are boxed and identical amino acids are both boxed and highlighted in black background. Gaps were introduced in dots.

FIG. 5B is an amino acid comparison between TIP1 (top) and *Caenorhabditis elegans* cAMP-dependent protein kinase catalytic subunit (PKAc). Lines represent identity and dots represent similarity.

Figure 6A:
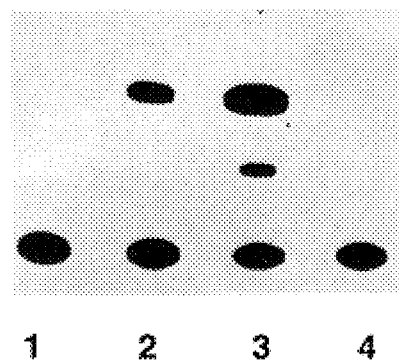

FIG. 6A shows the effects of TIP1 on transcription in vivo and the potentiation of Tat-activated gene expression by TIP1. HeLa cells were cotransfected with a HIV-1 LTR-CAT reporter plasmid p167, and plasmids expressing Tat and TIP1 as indicated. A typical result is shown on top.

Figure 6B:
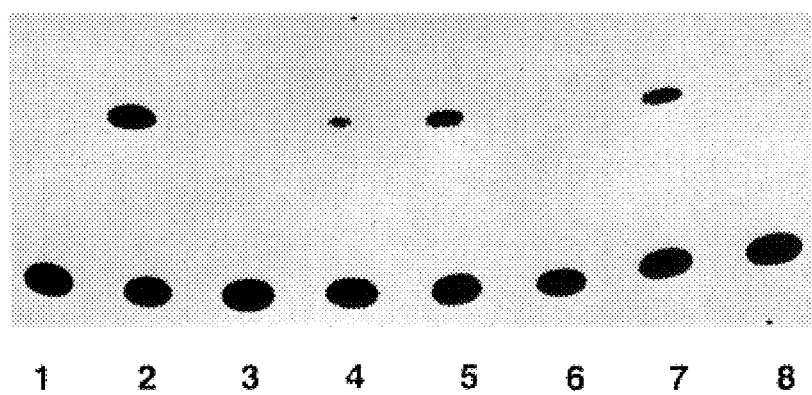

FIG. 6B shows the effects of TIP1 on transcription controlled by other activators. HeLa cells were cotransfected with a CAT reporter plasmid pG6-33HIVLTRΔTAR, and other plasmids as indicated. A typical result is shown on the bottom. LipofectAMINE (Giboco BRL) was used for transfection. CAT assays were performed as described below in Example 3. Acetylated and nonacetylated forms of [$^{14}$C] chloramphenicol were quantified by phosphorimager (Molecular dynamic Storm 840). Percent conversions of [$^{14}$C] chloramphenicol to acetylated forms were determined. The fold stimulation by TIP1 was determined from an average of at least three independent experiments.

Figure 7A:
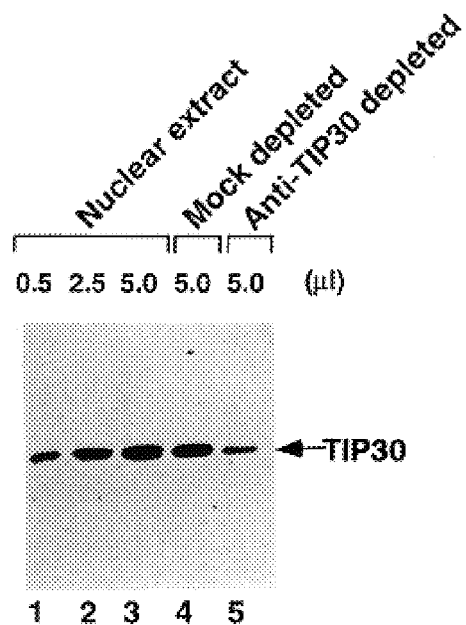

FIGS. 7A–D show that TIP1 is required specifically for the transactivation by Tat. FIG. 7A shows the immunodepletion of endogenous TIP1 from HeLa nuclear extract. HeLa nuclear extract in BC 100 plus 0.5 NaCI was passed through columns containing a Protein A-Sepharose and a Protein A-Sepharose cross-linked with anti-TIP1 antibody as described below in Example 3. The flow-through fractions were collected and dialyzed against BC100 for immunoblot and in vitro transcription assays. 5 μl of HeLa nuclear extract (lanes 3), mock-depleted (lane 4) and TIP1-depleted (lane 5) nuclear extract were immunoblotted with anti-TIP1 antibody. Lanes 1 and 2, 1 μl and 2.5 μl of HeLa nuclear extract. The arrowhead indicates the position of TIP1.

Figure 7B:
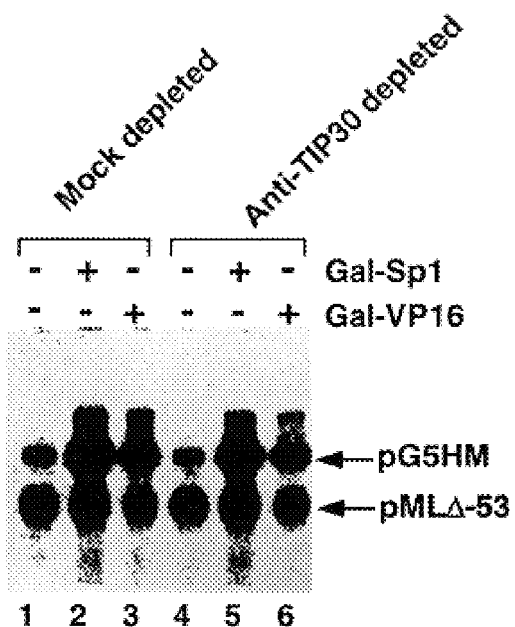

FIG. 7B shows the effect of TIP1 on transcriptional activation by Gal-VP16 and Gal-Sp1. 5 μl of mock-depleted or TIP1-depleted nuclear extracts were assayed for transcription in the absence (lanes 1 and 4) or presence of 10 ng of Gal-VP16 (lanes 2 and 5) and 20 ng of Gal-Sp1 (lanes 3 and 6), as indicated.

Figure 7C:
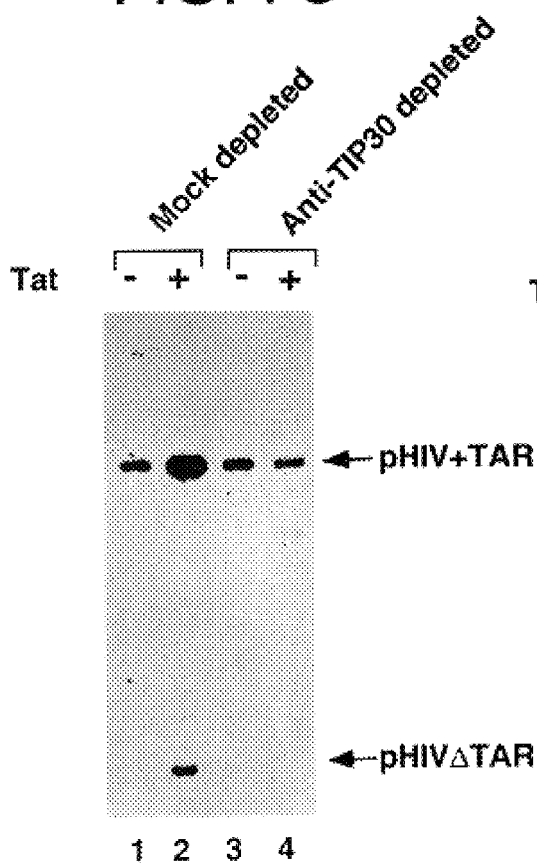

FIG. 7C shows the effect of TIP1 on transcriptional activation by Tat. 5 μl of mock-depleted or TIP1-depleted nuclear extract were assayed for transcription, as described below in Example 3, in the absence (lanes 1 and 3) or presence of 200 ng of Tat (lanes 2 and 4), as indicated. The arrowheads indicate the transcripts.

Figure 7D:
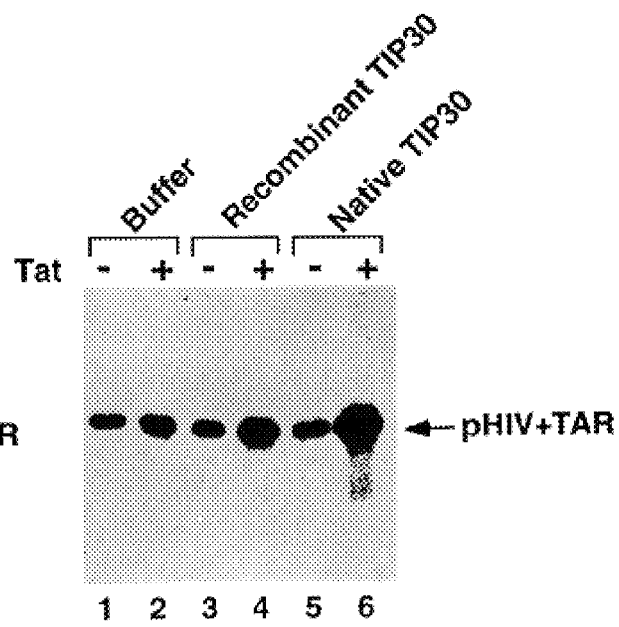

FIG. 7D shows the restoration of Tat activation by recombinant TIP1 and endogenous TIP1. The TIP1-depleted extracts supplemented with compensating buffer (lanes 1 and 2), 100 ng of recombinant TIP1 or 25 ng of endogenous TIP1 were assayed for their ability to support Tat-activated transcription, as described below in Example 3, as indicated.

FIGS. 8A and 8B show the DNA sequences for human TIP1 (SEQ ID NO:3) and mouse TIP2 (SEQ ID NO:4) respectively.

DETAILED DESCRIPTION

The present invention describes the isolation and purification of Tat-interacting proteins (TIPs), and methods of use therefor. These cofactors participate in the HIV-1 transcription process, and can be utilized in therapeutic and diagnostic methods relating to the treatment of AIDS.

One such TIP has been determined to be a novel cofactor having the following characteristics:

a) it binds with the activation domain of the HIV-1 regulatory protein Tat and specifically stimulates transactivation by Tat; and b) it possesses an apparent molecular weight of approximately 30 kDa as determined by SDS-polyacrylamide gel electrophoresis.

A further cofactor, designated herein as TIP2, and possessing an apparent molecular weight of approximately 56 kDa as determined by SDS-polyacrylamide gel electrophoresis, has also been isolated and characterized and determined to be the previously identified human cellular protein CD46.

Both of these cofactors can be utilized in the various methods of the present invention, since they bind to the activation domain of Tat (amino acids 1–48).

In a specific example, the Tat-interacting protein 30 (TIP30) of the present invention has the amino acid sequence as shown in FIG. 2A or 2E (SEQ ID NO: 1 or SEQ ID NO:2).

In a particular embodiment, the present invention relates to all members of the herein disclosed family of Tat-interacting proteins (TIPs).

The present invention also relates to a recombinant DNA molecule or cloned gene, or a degenerate variant thereof, which encodes a Tat-interacting protein 30 (TIP30); preferably a nucleic acid molecule, in particular a recombinant DNA molecule or cloned gene, encoding the Tat-interacting protein 30 (TIP30), and which has a nucleotide sequence or is complementary to a DNA sequence shown in FIGS. 8A and 8B (SEQ ID NO:3 and SEQ ID NO:4).

The human and murine DNA sequences of the Tat-interacting protein 30 (TIP30) of the present invention or portions thereof, may be prepared as probes to screen for complementary sequences and genomic clones in the same or alternate species. The present invention extends to probes so prepared that may be provided for screening cDNA and genomic libraries for the Tat-interacting protein 30 (TIP30). For example, the probes may be prepared with a variety of known vectors, such as the phage λ vector. The present invention also includes the preparation of plasmids including such vectors, and the use of the DNA sequences to construct vectors expressing antisense RNA or ribozymes which would attack the mRNAs of any or all of the DNA sequences set forth in FIGS. 8A and 8B (SEQ ID NO:3 and SEQ ID NO:4). Correspondingly, the preparation of antisense RNA and ribozymes are included herein.

The present invention also includes Tat-interacting protein 30 (TIP30) having the activities noted herein, and that display the amino acid sequences set forth and described above and selected from SEQ ID NO:1 and SEQ ID NO:2.

In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present Tat-interacting protein (TIP)(s), and more particularly, the complete DNA sequence determined from the sequences set forth above and in SEQ ID NO:3 and SEQ ID NO:4.

According to other preferred features of certain preferred embodiments of the present invention, a recombinant expression system is provided to produce biologically active animal or human Tat-interacting protein (TIP).

The concept of the Tat-interacting protein (TIP) contemplates that specific factors exist for correspondingly specific ligands, such as Tat-interacting protein (TIP) and the like, as described earlier. Accordingly, the exact structure of each Tat-interacting protein (TIP) will understandably vary so as to achieve this ligand and activity specificity. It is this specificity and the direct involvement of the Tat-interacting protein (TIP) in the chain of events leading to the level of transcription by Tat that offers the promise of a broad spectrum of diagnostic and therapeutic utilities.

The present invention naturally contemplates several means for preparation of the Tat-interacting proteins (TIPs), including as illustrated herein known recombinant techniques, and the invention is accordingly intended to cover such synthetic preparations within its scope. The isolation of the cDNA and amino acid sequences disclosed herein facilitates the reproduction of the Tat-interacting proteins (TIPs) by such recombinant techniques, and accordingly, the invention extends to expression vectors prepared from the disclosed DNA sequences for expression in host systems by recombinant DNA techniques, and to the resulting transformed hosts.

The invention includes an assay system for screening of potential drugs effective to modulate Tat-interacting proteins (TIPs) activity of target mammalian cells by interrupting or potentiating the Tat-interacting proteins (TIPs). In one instance, the test drug could be administered to a cellular sample with the ligand that activates the Tat-interacting proteins (TIPs), or an extract containing the activated Tat-interacting proteins (TIPs), to determine its effect upon the binding activity of the Tat-interacting proteins (TIPs) to any chemical sample (including DNA), or to the test drug, by comparison with a control.

The assay system could more importantly be adapted to identify drugs or other entities that are capable of binding to the Tat-interacting proteins (TIPs), either in the cytoplasm or in the nucleus, thereby inhibiting or potentiating the level of transcription of Tat. Such an assay would be useful in the development of drugs that would be specific against the particular cellular activity, or that would potentiate such activity, in time or in level of activity. For example, such drugs might be used to decrease or prevent the replication of the HIV-1 virus in its host organism.

In yet a further embodiment, the invention contemplates antagonists of the activity of a Tat-interacting protein (TIP). In particular, an agent or molecule that inhibits Tat-interacting protein 30 (TIP30). In a specific embodiment, the antagonist can be a peptide having the sequence of a portion of the binding domain of the Tat-interacting protein 30 (TIP30) which binds to the Tat protein.

One of the characteristics of the present Tat-interacting protein 30 (TIP30) is its function as a cofactor that interacts with the activation domain of Tat, thereby participating in the increase in the level of transcription by the HIV-1 regulatory protein Tat.

The diagnostic utility of the present invention extends to the use of the present Tat-interacting proteins (TIPs) in assays to screen for Tat-interacting proteins (TIPs).

The present invention likewise extends to the development of antibodies against the Tat-interacting proteins (TIPs), including naturally raised and recombinantly prepared antibodies. For example, the antibodies could be used to screen expression libraries to obtain the gene or genes that encode the Tat-interacting protein 30 (TIP30). Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating Tat-interacting protein 30 (TIP30) activity.

In particular, antibodies against specifically phosphorylated factors can be selected and are included within the scope of the present invention for their particular ability in following activated protein. Thus, activity of the Tat-interacting protein (TIP) or of the specific polypeptides believed to be causally connected thereto may therefore be followed directly by the assay techniques discussed later on, through the use of an appropriately labeled quantity of the Tat-interacting protein (TIP) or antibodies or analogs thereof.

Thus, the Tat-interacting proteins (TIPs), their analogs and/or analogs, and any antagonists or antibodies that may be raised thereto, are capable of use in connection with various diagnostic techniques, including immunoassays, such as a radioimmunoassay, using for example, an antibody to the Tat-interacting protein (TIP) that has been labeled by either radioactive addition, or radioiodination.

In an immunoassay, a control quantity of the antagonists or antibodies thereto, or the like may be prepared and labeled with an enzyme, a specific binding partner and/or a radioactive element, and may then be introduced into a cellular sample.

After the labeled material or its binding partner(s) has had an opportunity to react with sites within the sample, the resulting mass may be examined by known techniques, which may vary with the nature of the label attached. For example, antibodies against specifically phosphorylated factors may be selected and appropriately employed in the exemplary assay protocol, for the purpose of following activated protein as described above.

In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The present invention includes an assay system which may be prepared in the form of a test kit for the quantitative analysis of the extent of the presence of the Tat-interacting protein (TIP), or to identify drugs or other agents that may mimic or block their activity. The system or test kit may comprise a labeled component prepared by one of the radioactive and/or enzymatic techniques discussed herein, coupling a label to the Tat-interacting protein (TIP), their agonists and/or antagonists, and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the Tat-interacting protein (TIP)(s), its (or their) subunits, or active fragments thereof, or upon agents or other drugs determined to possess the same activity. A first therapeutic method is associated with the prevention of the manifestations of conditions causally related to or following from the binding activity of the Tat-interacting protein (TIP) or its subunits, and comprises administering an agent capable of modulating the production and/or activity of the Tat-interacting protein (TIP) or subunits thereof, either individually or in mixture with each other in an amount effective to prevent the development of those conditions in the host. For example, drugs or other binding partners to the Tat-interacting protein (TIP) or proteins may be administered to inhibit Tat-interacting protein (TIP) activity, as in the inhibition of Tat-interacting protein (TIP) in anti-HIV-1 therapy. Also, the increase of the action of specific tyrosine phosphatases in the phosphorylation of activated (phosphorylated) Tat-interacting protein (TIP) or proteins presents a method for inhibiting the activity of the Tat-interacting protein (TIP) or protein that would concomitantly provide a therapy based on Tat-interacting protein (TIP)/protein inactivation.

More specifically, the therapeutic method generally referred to herein could include the method for the treatment of various pathologies or other cellular dysfunctions and derangements by the administration of pharmaceutical compositions that may comprise effective inhibitors of activation of the Tat-interacting protein (TIP) or its subunits, or other equally effective drugs developed for instance by a drug screening assay prepared and used in accordance with a further aspect of the present invention. For example, drugs or other binding partners to the Tat-interacting protein 30 (TIP30) or proteins, as represented by SEQ ID NO:1, may be administered to inhibit Tat-interacting protein 1 (TIP) activity. Also, an increase of the action of specific tyrosine phosphatases in the dephosphorylation of activated Tat-interacting proteins (TIPs) presents a method for inhibiting or decreasing the activity of the Tat-interacting proteins (TIPs) that would concomitantly potentiate therapies based on Tat-interacting protein (TIP) deactivation.

In particular, the Tat-interacting proteins whose sequences are presented in SEQ ID NO:1 herein, their antibodies, agonists, antagonists, or active fragments thereof, could be prepared in pharmaceutical formulations for administration in instances wherein anti-HIV-1 therapy is appropriate.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation"[B. D. Hames & S. J. Higgins, eds. (1984)]; "Animal Cell Culture" [R. I. Freshney, ed. (1986)]; "Immnobilized Cells And Enzymes" [IRL Press, (1986)]; B. Perbal, "A Practical Guide To Molecular Cloning" (1984).

Therefore, if appearing herein, the following terms shall have the definitions set out below.

The terms "Tat-interacting protein, "TIP" and any variants not specifically listed, may be used herein interchangeably, and as used throughout the present application and claims refer to proteinaceous material including single or multiple proteins, and extends to those proteins having the amino acid sequence data described herein and presented in FIG. 2A and 2E (SEQ ID NOS:1 and 2), and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "Tat-interacting protein", "TIP" and "TIP(s)" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552–59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the ukaryotic cell to establish cell lines or clones comprised of a population of daughter ells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences which code for a Tat-interacting protein (TIP) having the same amino acid sequence as SEQ ID NOS:1 and 2, but which are degenerate to SEQ ID NO:2. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in SEQ ID NOS:3 and 4 such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino acids with nonpolar R groups

Alanine

Valine

Leucine

Isoleucine

Proline

Phenylalanine

Tryptophan

Methionine

Amino acids with uncharged polar R groups

Glycine

Serine

Threonine

Cysteine

Tyrosine

Asparagine

Glutamine

Amino acids with charged polar R groups (negatively charged at Ph 6.0)

Aspartic acid

Glutamic acid

Basic amino acids (positively charged at pH 6.0)

Lysine

Arginine

Histidine (at pH 6.0)

Another grouping may be those amino acids with phenyl groups:
Phenylalanine
Tryptophan
Tyrosine Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:
—Lys for Arg and vice versa such that a positive charge may be maintained;
—Glu for Asp and vice versa such that a negative charge may be maintained;
—Ser for Thr such that a free —OH can be maintained; and
—Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', $F(ab')_2$ and F(v), which portions are preferred for use in the therapeutic methods described herein.

Fab and $F(ab')_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab') portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the activity of the HIV infection.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA—RNA, DNA—DNA or RNA-DNA. Such standard hybridization conditions are easily determined by one skilled in the art according to well known formulae, wherein hybridization is typically 10–20° C. below the predicted or determined $T_m$ with washes of higher stringency, if desired.

In its primary aspect, the present invention concerns the identification of Tat-interacting proteins (TIPs).

In a particular embodiment, the present invention relates to all members of the herein disclosed Tat-interacting proteins (TIPs), and especially to the novel Tat-interacting protein 30 (TIP30).

As stated above, the present invention also relates to a recombinant DNA molecule or cloned gene, or a degenerate variant thereof, which encodes a Tat-interacting protein (TIP), or a fragment thereof, that possesses a molecular weight of about 30 kD and an amino acid sequence set forth in FIG. 2A and 2E (SEQ ID NOS:1 and 2); preferably a nucleic acid molecule, in particular a recombinant DNA molecule or cloned gene, encoding the 30 kD Tat-interacting protein (TIP), has a nucleotide sequence or is complementary to a DNA sequence shown in FIGS. 8A and 8B (SEQ ID NOS:3 and 4).

The possibilities both diagnostic and therapeutic that are raised by the existence of the Tat-interacting protein (TIPs), derive from the fact that the factors appear to participate in direct and causal protein-protein interaction between the (Tat-interacting protein (TIPs), and those factors that thereafter interact with the activation domain of Tat and thereby increase transcription. As suggested earlier and elaborated further on herein, the present invention contemplates pharmaceutical intervention in the cascade of reactions in which the Tat-interacting protein (TIPs) are implicated, to modulate the activity initiated by the (Tat-interacting protein (TIPs).

Thus, in instances where it is desired to reduce or inhibit the (resulting from a particular stimulus or factor, an appropriate inhibitor of the Tat-interacting protein (TIP) could be introduced to block the interaction of the Tat-interacting protein (TIP) with Tat thereby affecting its transcription rate.

As discussed earlier, agents exhibiting antagonism to the Tat-interacting protein (TIP) or control over production, may be prepared in pharmaceutical compositions, with a suitable carrier and at a strength effective for administration by various means to a patient experiencing an adverse medical condition associated with HIV-1 infection for the treatment thereof. A variety of administrative techniques may be utilized, among them parenteral techniques such as subcutaneous, intravenous and intraperitoneal injections, catheterizations and the like. Average quantities of the antagonist of the Tat-interacting protein (TIP) or their subunits may vary and in particular should be based upon the recommendations and prescription of a qualified physician or veterinarian.

Also, antibodies including both polyclonal and monoclonal antibodies, and drugs that modulate the production or activity of the Tat-interacting proteins (TIPs) and/or their subunits may possess certain diagnostic applications and may for example, be utilized for the purpose of detecting and/or measuring conditions such as HIV-1 infection or the like. For example, the Tat-interacting proteins (TIPs) or their subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the Tat-interacting proteins (TIPs) of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also, U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against Tat-interacting protein (TIP) peptides can be screened for various properties; i.e., isotype, epitope, affinity, etc. Of particular interest are monoclonal antibodies that neutralize the activity of the Tat-interacting protein (TIP) or its subunits. Such monoclonals can be readily identified in Tat-interacting protein (TIP) activity assays. High affinity antibodies are also useful when immunoaffinity purification of native or recombinant Tat-interacting protein (TIP) is possible.

Preferably, the anti-Tat-interacting protein (TIP) antibody used in the diagnostic methods of this invention is an affinity purified polyclonal antibody. More preferably, the antibody is a monoclonal antibody (mAb). In addition, it is preferable for the anti-Tat-interacting protein (TIP) antibody molecules used herein be in the form of Fab, Fab', $F(ab')_2$ or F(v) portions of whole antibody molecules.

As suggested earlier, the diagnostic method of the present invention comprises examining a cellular sample or medium by means of an assay including an effective amount of an antagonist to a Tat-interacting protein (TIP)/protein, such as an anti-Tat-interacting protein (TIP) antibody, preferably an affinity-purified polyclonal antibody, and more preferably a mAb. In addition, it is preferable for the anti-Tat-interacting protein (TIP) antibody molecules used herein be in the form of Fab, Fab', $F(ab')_2$ or F(v) portions or whole antibody molecules. As previously discussed, patients capable of benefiting from this method include those suffering from an HIV-1 infection or other like pathological derangement. Methods for isolating the Tat-interacting protein (TIP) and inducing anti-Tat-interacting protein (TIP) antibodies and for determining and optimizing the ability of anti-Tat-interacting protein (TIP) antibodies to assist in the examination of the target cells are all well-known in the art.

Methods for producing polyclonal anti-polypeptide antibodies are well-known in the art. See U.S. Pat. No. 4,493,795 to Nestor et al. A monoclonal antibody, typically containing Fab and/or $F(ab')_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a Tat-interacting protein (TIP)-binding portion thereof, or Tat-interacting protein (TIP), or an origin-specific DNA-binding portion thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present Tat-interacting protein (TIP) and their ability to inhibit specified TIP activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal anti-Tat-interacting protein (TIP) antibodies are also well-known in the art. See Niman et al., *Proc. Natl. Acad. Sci.* USA, 80:4949–4953 (1983). Typically, the present Tat-interacting protein (TIP) or a peptide analog is used either alone or conjugated to an immunogenic carrier, as the immunogen in the before described procedure for producing anti-Tat-interacting protein (TIP) monoclonal antibodies. The hybridomas are screened for the ability to produce an antibody that immunoreacts with the Tat-interacting protein (TIP) peptide analog and the present Tat-interacting protein (TIP).

The present invention further contemplates therapeutic compositions useful in practicing the therapeutic methods of this invention. A subject therapeutic composition includes, in admixture, a pharmaceutically acceptable excipient (carrier) and one or more of a Tat-interacting protein (TIP), polypeptide analog thereof or fragment thereof, as described herein as an active ingredient. In a preferred embodiment, the composition comprises an antigen capable of modulating the specific binding of the present Tat-interacting protein (TIP) within a target cell.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of Tat-interacting protein (TIP) binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The therapeutic compositions may further include an effective amount of the Tat-interacting protein (TIP) antagonist, and one or more of the following active ingredients: an antibiotic, a steroid. Exemplary formulations are given below:

| Formulations | |
|---|---|
| Ingredient | mg/ml |
| Intravenous Formulation I | |
| cefotaxime | 250.0 |
| Tat-interacting protein (TIP) antagonist | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation II | |
| ampicillin | 250.0 |
| Tat-interacting protein (TIP) antagonist | 10.0 |
| sodium bisulfite USP | 3.2 |
| disodium edetate USP | 0.1 |
| water for injection q.s.a.d. | 1.0 ml |
| Intravenous Formulation III | |
| gentamicin (charged as sulfate) | 40.0 |
| Tat-interacting protein (TIP) antagonist | 10.0 |
| sodium bisulfite USP | 3.2 |
| disodium edetate USP | 0.1 |
| water for injection q.s.a.d. | 1.0 ml |
| Intravenous Formulation IV | |
| Tat-interacting protein (TIP) antagonist | 10.0 |
| dextrose USP | 45.0 |
| sodium bisulfite USP | 3.2 |

| Formulations | |
|---|---|
| Ingredient | mg/ml |
| edetate disodium USP | 0.1 |
| water for injection q.s.a.d. | 1.0 ml |
| Intravenous Formulation V | |
| Tat-interacting protein (TIP) antagonist | 5.0 |
| sodium bisulfite USP | 3.2 |
| disodium edetate USP | 0.1 |
| water for injection q.s.a.d. | 1.0 ml |

As used herein, "pg" means picogram, "ng" means nanogram, "ug" or "µg" mean microgram, "mg" means milligram, "ul" or "µl" mean microliter, "ml" means milliliter, "1" means liter.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2µ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, R1.1, B–W and L–M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that Tat-interacting protein (TIP) analogs may be prepared from nucleotide sequences of the protein complex/subunit derived within the scope of the present invention. Analogs, such as fragments, may be produced, for example, by pepsin digestion of Tat-interacting protein (TIP) material. Other analogs, such as muteins, can be produced by standard site-directed mutagenesis of Tat-interacting protein (TIP) coding sequences. Analogs exhibiting "Tat-interacting protein (TIP) activity" such as small molecules, whether functioning as promoters or inhibitors, may be identified by known in vivo and/or in vitro assays.

As mentioned above, a DNA sequence encoding Tat-interacting protein (TIP) can be prepared synthetically rather than cloned. The DNA sequence can be designed with the appropriate codons for the Tat-interacting protein (TIP) amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311 (1984).

Synthetic DNA sequences allow convenient construction of genes which will express Tat-interacting protein (TIP) analogs or "muteins". Alternatively, DNA encoding muteins can be made by site-directed mutagenesis of native Tat-interacting protein (TIP) genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, Science, 244:182–188 (April 1989). This method may be used to create analogs with unnatural amino acids.

The present invention extends to the preparation of antisense oligonucleotides and ribozymes that may be used to interfere with the expression of the Tat-interacting protein (TIP) at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into Tat-interacting protein (TIP)-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, Tetrahymena-type and "hammerhead"-type. (Hasselhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs for Tat-interacting protein (TIP) and their ligands.

The present invention also relates to a variety of diagnostic applications, including methods for detecting the presence of stimuli such as the earlier referenced polypeptide ligands, by reference to their ability to elicit the activities which are mediated by the present Tat-interacting protein (TIP). As mentioned earlier, the Tat-interacting protein (TIP) can be used to produce antibodies to itself by a variety of known techniques, and such antibodies could then be isolated and utilized as in tests for the presence of particular Tat-interacting protein (TIP) activity in suspect target cells.

As described in detail above, antibody(ies) to the Tat-interacting protein (TIP) can be produced and isolated by standard methods including the well known hybridoma techniques. For convenience, the antibody(ies) to the Tat-interacting protein (TIP) will be referred to herein as $Ab_1$ and antibody(ies) raised in another species as $Ab_2$.

The presence of Tat-interacting protein (TIP) in cells can be ascertained by the usual immunological procedures applicable to such determinations. A number of useful procedures are known. Three such procedures which are especially usefull utilize either the Tat-interacting protein (TIP) labeled with a detectable label, antibody $Ab_2$. labeled with a detectable label, or antibody $Ab_2$ labeled with a detectable label. The procedures may be summarized by the following equations wherein the asterisk indicates that the particle is labeled, and TIP stands for the Tat-interacting protein:

A. $TIP^* + Ab_1 TIP^* Ab_1$

B. $TIP + Ab^* = TIPAb_1^*$

C. $TIP + Ab_1 + Ab_2^* = TIPAb_1 Ab_2^*$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASP" procedure.

In each instance, the Tat-interacting protein (TIP) forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-Tat-interacting protein (TIP) antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The Tat-interacting protein (TIP) or its binding partner(s) can also be labeled with a radioactive element or with an enzyme. The radioactive label can be detected by any of the currently available counting procedures. The preferred isotope may be elected from $3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise usefull, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the Tat-interacting protein (TIP) may be radiolabeled and combined, for example, with antibodies or other inhibitors thereto, after which binding studies would be carried out. Solutions would then be prepared that contain various quantities of labeled and unlabeled uncombined Tat-interacting protein (TIP), and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

An assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

In a further embodiment of this invention, commercial test kits suitable for use by a medical specialist may be prepared to determine the presence or absence of predetermined Tat-interacting protein (TIP) activity or predetermined Tat-interacting protein (TIP) activity capability in suspected target cells. In accordance with the testing techniques discussed above, one class of such kits will contain at least the labeled Tat-interacting protein (TIP) or its binding partner, for instance an antibody specific thereto, and directions, of course, depending upon the method selected, e.g., "competitive," "sandwich," "DASP" and the like. The kits may also contain eripheral reagents such as buffers, stabilizers, etc.

Accordingly, a test kit may be prepared for the demonstration of the presence or capability of cells for predetermined Tat-interacting protein (TIP) activity, comprising:

(a) a predetermined amount of at least one labeled immunochemically reactive component obtained by the direct or indirect attachment of the present Tat-interacting protein (TIP) factor or a specific binding partner thereto, to a detectable label;

(b) other reagents; and (c) directions for use of said kit.

More specifically, the diagnostic test kit may comprise:

(a) a known amount of the Tat-interacting protein (TIP) as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive," "sandwich," "double antibody," etc.), and comprises:

(a) a labeled component which has been obtained by coupling the Tat-interacting protein (TIP) to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the Tat-interacting protein (TIP) and a specific binding partner thereto.

In accordance with the above, an assay system for screening potential drugs effective to modulate the activity of the Tat-interacting protein (TIP) may be prepared. The Tat-interacting protein (TIP) may be introduced into a test system, and the prospective drug may also be introduced into the resulting cell culture, and the culture thereafter examined to observe any changes in the Tat-interacting protein (TIP) activity of the cells, due either to the addition of the prospective drug alone, or due to the effect of added quantities of the known Tat-interacting protein (TIP).

PRELIMINARY CONSIDERATIONS

The following examples are presented in order to more fully illustrate the preferred embodiments of the invention. They should in no way be construed, however, as limiting the broad scope of the invention.

EXAMPLE 1

To identify cellular proteins that interact with the activation domain of Tat, fusion protein [GST-Tat(1–48)] containing the amino-terminal 48 amino acids of HIV-1 Tat was used for protein affinity chromatography (Blau et al., *Mol. Cell. Biol.* 16, 2044 (1996)). The bacterially expressed fusion protein was bound to Glutathione-Sepharose and used as a ligand (Xiao et al., *Mol. Cell. Biol.* 14, 7013 (1994)). As controls, two GST-Tat (1–48) fusion proteins containing amino acid substitutions K41T and F38A within the activation domain were also used as ligands.

The plasmid pGEX-3X-Tat (1–48) was described previously in Blau et al. supra. The pGEX-3X-Tat (1–48K41T) and pGEX-3X-Tat (1–48F38A) used for expression of mutant GST-Tat proteins were constructed by digesting the plasmids pGEX-3X-Tat K41T and pGEX-3X-TatF38A with EagI and EcoRI, filling in and recircularizing. To construct the series of mutant GST-Tat plasmids, Tat coding sequence (amino acids 1–72) was first cloned into Bluescript (+) (Stratagene) and mutations were introduced at positions 41 and 38 by using oligonucleotide-directed mutagenesis (Amersham). Afterwards, the Tat coding sequences containing mutations were cloned into pGEX-3X in-frame with the glutathione S-transferase gene. HeLa whole cell extract was prepared as described previously in Xiao et al., supra. To purify Tat-binding proteins on a large scale, 100 ml of HeLa whole cell extract (5 mg/ml protein) were chromatographed on a 5 ml GST-Tat (1–48) affinity column. The bound proteins were eluted with 20 ml of 1 M NaCl in ACB and dialyzed against 0.1 M NaCl in ACB. 15 ml of the dialyzed bound proteins were loaded onto a 0.5 ml phosphocellulose column and step eluted with 2.5 ml each 0.3, 0.5 and 0.85 M NaCl in ACB. 20 µl aliquots of the eluted fractions (0.5 ml) were first analyzed by SDS-PAGE and stained with silver. The 30 kDa protein was present in the 0.3 M NaCl fraction. The 0.3 M NaCl fractions were pooled. The proteins were precipitated with trichloroacetic acid and loaded onto an SDS-polyacrylamide gel. The 30 kDa band was visualized by staining with Commassie blue and excised from the gel. The proteins were digested with endoproteinase C. The resulting peptides were isolated by HPLC and subjected to microsequencing.

Figure 1:
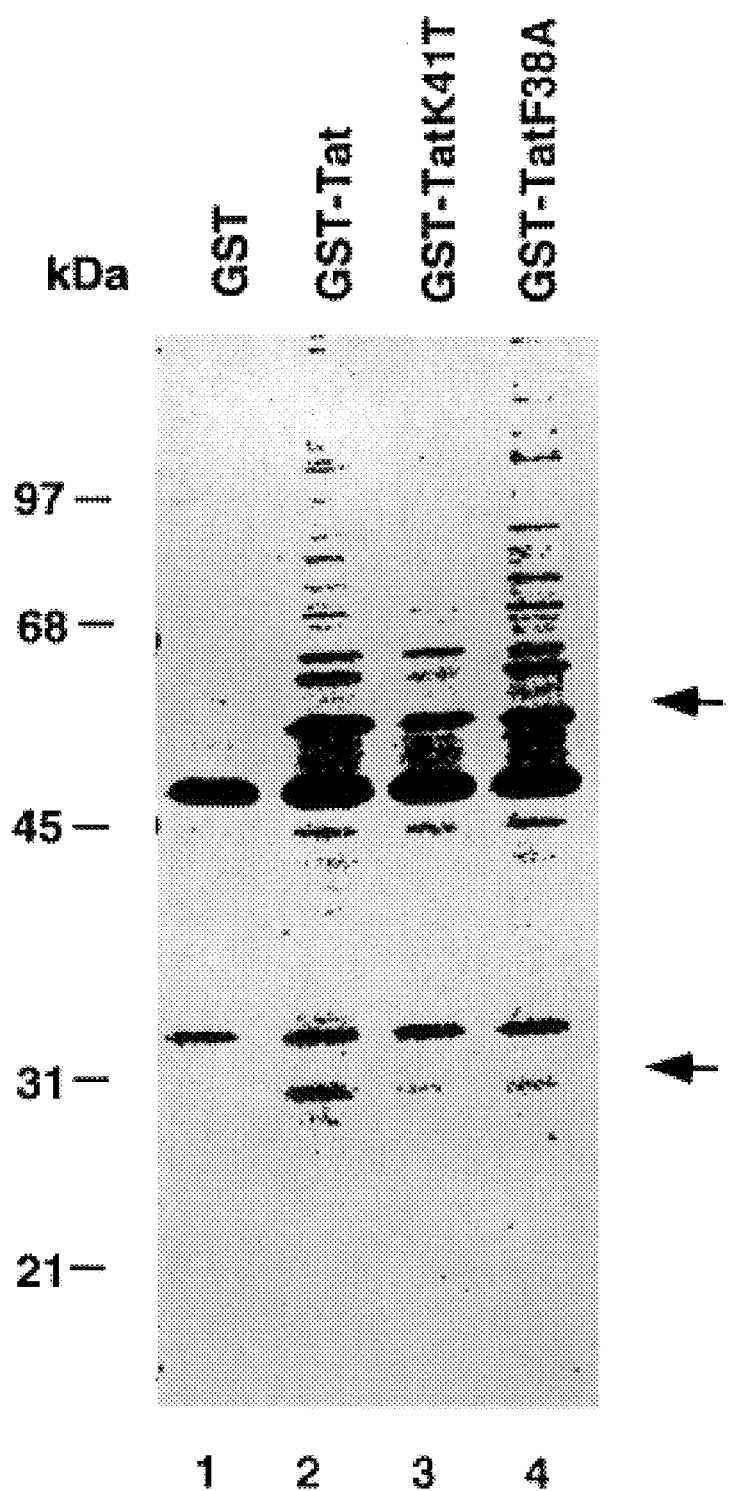

Both amino acid substitutions significantly weaken transcriptional activation by GAL4-Tat(1–48), indicating that they might interrupt the interaction between Tat and its cofactor(s) (Kamine et al., Proc. Natl. Acad. Sci. USA 88, 8510 (1991)). To carry out affinity chromatography, a HeLa whole cell extract was loaded onto the columns at 100 mM NaCl and washed at 100 mM NaCl. Bound proteins were eluted with buffer containing 1 M NaCl, resolved by SDS-polyacrylamide gel electrophoresis and stained with silver. Two polypeptides with apparent molecular masses of 30 kDa and 56 kDa selectively bound to the GST-Tat(1–48) (FIG. 1, lane 2) column, but not to the GST column (FIG. 1, lane 1). These two polypeptides bound less efficiently to the GST-Tat mutant columns (compare FIG. 1, lane 2 with lanes 3 and 4), indicating that interactions between the activation domain of Tat and the two proteins are biologically important. Binding of the 30 kDa and 56 kDa proteins when HeLa nuclear extracts were subjected to Tat affinity chromatography was also observed (data not shown). The 30 kDa protein has been designated as Tat-interacting protein 30 (TIP30) and the 56 kDa protein as Tat-interacting protein 2 (TIP2).

In order to further characterize TIP1, the Tat bound proteins from a large scale GST-Tat(1–48) affinity chromatography preparation were fractionated by phosphocellulose chromatography (TIP1) eluted at 0.3 M KCl) and SDS-polyacrylamide gel electrophoresis. TIP1 was excised and digested with proteinase and derived peptides were separated by HPLC and microsequenced. Of the seven peptide sequences obtained from TIP1, five matched amino acid sequences encoded by a randomly cloned human cDNA in the EST database. The subsequent sequence analysis of a 1.2 kB insertion revealed an open reading frame encoding a 242 amino acid protein with a calculated mass of 27.3 kDa and an estimated isoelectric point of 9.01 (FIG. 2A SEQ ID NO:1). All seven of the original peptide sequences were found within this open reading frame (2a, underlined sequences), which appears to contain full-length TIP1 for the following reasons. First, there is a good match to the consensus Kozak sequence (CCA/GCCATGG) of the first AUG (Kozak, Cell 44, 283 (1986)); the nucleotide at −3 position is a G and the nucleotide at position +4 is G. Second, a search of the database with the entire TIP1 sequence resulted in the identification of 15 related cDNA clones derived from several libraries. An in-frame stop codon located 30 base pairs upstream of the first ATG codon was found in a cDNA clone derived from Pancreatic islet. Moreover, the nucleotide sequences upstream of the first ATG codon of the cDNA clones derived from heart, colon, endothelial cell, pancreatic islet cells and NT2 neuronal precursor cDNA libraries were varied (data not shown), suggesting that distinctive splicing sites upstream of the first ATG codon may create distinctive 5' untranslated sequences of TIP1 transcripts in different tissues. Third, the size of recombinant protein is indistinguishable from that of endogenous TIP1 of HeLa nuclear extract.

For expressing TIP1 in bacteria and generating polyclonal antibodies against TIP1, a PCR-based method was used to generate a TIP1 cDNA containing an NdeI site at the N-terminal end and a BamHI site at the C-terminal end following the stop codon. The resulting PCR product was subcloned into the 6HisT-pRSET (Hoffman et al., J. Biol. Chem. 271, 18194 (1996)). His-tagged TIP1 protein expressed in bacteria was purified and then used for immunization of rabbits as described previously (Tong et al., J. Biol. Chem. 272, 6714 (1997)). HeLa nuclear extract was prepared as described by Chiang et al., EMBO J. 12, 2749 (1993)). For in vitro transcription/translation, the plasmid pET 11 aTIP 1 was used to produce TIP 1. This plasmid was constructed by insertion of a 730 bp DNA fragment, which was isolated by digestion of 6HisT-pRSETTIP1 with NdeI and BamHI, into pET11 a (Novgen). The plasmid pRSETTat used for producing Tat was constructed by inserting a BglII Tat cDNA fragment (encoding 1–72 amino acids) into the BamdH1 site of pRSET-C (Invitrogen). [$^{35}$S]methionine labeled TIP1 and Tat were made in the Promega TNT reticulocyte lysate system according to the manufacturer's instructions. For bead pull-down assays, a plasmid encoding GST-TIP1 was constructed by inserting TIP1 cDNA (NdeI and BamH DNA fragment) into pGEX-2TL+(28). [$^{35}$S] methionine-labeled Tat was incubated with glutathione-Sepharose beads containing GST and GST-TIP1 (2 mg/ml) in BC 100 buffer containing 0.1% NP40. The beads were washed extensively with BC100 buffer containing 0.1% NP40 and then boiled in the protein sample buffer for 2 minutes.

To show this, a bacterially expressed TIP1 protein was used to raise a rabbit polyclonal antibody that specifically detects a 30 kDa protein from HeLa nuclear extract, a DNA template containing TIP1 cDNA under the control of a T7 promoter was used to express a recombinant $^{35}$S-labeled protein in an in vitro transcription/translation system. In vitro translated and HeLa nuclear extract proteins were resolved by SDS-polyacrylamide gel electrophoresis, then transferred on nitrocellulose membrane, and subjected to anti-TIP1 immunoblot a nd autoradiographic analysis. As shown in 2B, the $^{35}$S-labeled recombinant protein comigrates with the endogenous TIP1 in HeLa nuclear extract (Lane 2). The smaller polypeptide (Lane 2) may be either a truncated TIP1 resulting from an internal translation start site or a proteolytic product. Finally, as shown below, the recombinant TIP1 has transcriptional activity.

EXAMPLE 2

To further ascertain that the cDNA encodes authentic TIP1, the eluates from GST and GST-Tat(1–48) columns were immnunoblotted with anti-TIP1 antibody (FIG. 2C). An immunoreactive polypeptide, identical in size to TIP1 in the nuclear extract (FIG. 2C, lane 1), was detected in the eluate from the affinity column containing the Tat activation domain (lane 3) but not in the eluates from the control column containing GST (lane 2). Moreover, in vitro translated Tat labeled with $^{35}$S-methionine was bound to the GST-TIP1 fusion protein (FIG. 2D).

To determine the tissue distribution of the TIP1 mRNA, Northern blot analysis on total poly A+RNAs from human tissues was performed. Consistent with the size of the TIP1 cDNA, a single 1.4 kb transcript was detected in multiple tissues (FIG. 3). The level of TIP1 mRNA varies only moderately in the different tissues, with the exception of brain tissue in which the level is approximately 10 times lower than the level in liver and placenta tissues (FIG. 3).

Since the activation domain of Tat has been found to interact with several cellular proteins that appear to be present in relatively large complexes, further purification of TIP1 for functional assays and determination of its native size was attempted. To this end, Tat bound proteins were fractionated on a gel filtration column and the resulting fractions were analyzed by SDS-polyacrylamide gel electrophoresis followed by silver staining and by Western blot analysis. By this analysis, TIP1 appears to have a native size of approximate 25 kDa (FIG. 4).

By database searches with the entire deduced amino acid sequence of TIP1, a Caenorhabditis elegans hypothetical protein was identified that may be the counterpart of TIP1. This hypothetical protein is similar to *E. coli* ORF-f226 and yeast hypothetical protein YEJ4 (FIG. 5A). Human TIP1 is 34% identical and 55% similar in amino acid sequence to the *Caenorhabditis elegans* hypothetical protein. Human TIP1 and yeast YEJ4 show an overall amino acid identity of 28% and a similarity of 45%. Interestingly, the amino terminal 20 amino acids of the human TIP1 are unrelated to those in *E. coli* ORF-f226 and completely missing in Caenorhabditis elegans hypothetical protein and yeast YEJ4, suggesting that this region may be acquired in evolution to possess a specific function.

In addition, it has also been found that TIP1 shares significant similarities with a cAMP-dependent protein kinase catalytic subunit (50% similarity and 23% identity) as shown in FIG. 5B. This indicates that TIP1 might be a protein kinase. Although phosphorylation of TIP1 was detected by incubating highly purified recombinant TIP1 from bacteria with [$\gamma^{32}$P]-ATP (data not shown), detection of the autophosphorylation of TIP1 by following denaturation/renaturation of TIP1 from SDS-polyacrylamide gels was not shown.

EXAMPLE 3

The specific binding of TIP1 to the activation domain of Tat indicates the role of TIP1 in transcriptional activation by Tat. To examine this, HeLa cells were cotransfected with a plasmid (pcDNA3. 1TIP1), that contains TIP1 cDNA under the control of a CMV promotor, a plasmid containing a chloramphenicol acetyltransferase (CAT) gene under the control of the HIV-1 long terminal repeat (LTR) and a plasmid (pSVtat), that expresses HIV-1 Tat (Emerman et al., *EMBO J.* 6, 3755 (1987)).

For transfection assays, TIP1 cDNA was subcloned into the mammalian expression vector pcDNA3.1 (Novgen) to create pcDNA3.1 TIP1. The plasmids pGal-VP16 and pGal-E1A, pGal-p53 (Fields et al., *Science* 249, 1046 (1990)), pSVTat (Emerman et al.), p167 (Marciniak et al., *Cell* 63, 791 (1990)) have been previously described. The transfection were performed as described by manufacturer's instruction (Giboco BRL). Cell lysates were first assayed for β-galactosidase activity (Suen et al., *Mol. Cell. Biol.* 11, 354 (1991)). Normalized quantities of cell extracts were then analyzed by thin-layer CAT assays. No significant effect on expression of the CAT gene was observed when TIP1 was expressed in the absence of Tat (FIG. 6A). However, overexpression of TIP1 increased Tat-activated transcription by approximate 9-fold (8.9 ±3, means±SEM, n=4).

It was also tested as to whether TIP1 can increase transactivation by other transactivators. As shown in FIG. 6B, TIP1 did not affect significantly the expression of CAT from an HIV-LTR reporter containing Ga14 binding sites when pcDA3.1TIP1 was cotransfected with vectors expressing Gal-VP16, Gal-p53 or Gal-E1A. This has been consistently observed in three independent experiments.

To directly assess whether TIP1 is required for both basal and activated transcription, antigen-purified anti-TIP1 antibody was used to immunodeplete TIP1 from HeLa nuclear extracts.

For immunodepletion of TIP1, anti-TIP1 sera were purified by passage through a column containing His-tagged TIP1 protein. The anti-TIP1 antibodies were eluted with 200 mM glycine pH 2.5. The antibodies were further purified by binding to protein A-Sepharose (Pharmacia) and then cross-linked with dimethylpimilidate. 400 μl of HeLa nuclear extract in BC100 adjusted to 0.5 M NaCl were passed through 100 μl of crossed-linked anti-TIP1 protein A-Sepharose or protein A-Sepharose columns for 5 times and the flow-through fractions were used for Western blotting and in vitro transcription analyses. In vitro transcription with Gal-VP16 and Gal-Sp1 were performed as described previously. Gal-VP16 and Gal-Sp1 were purified as previously described. In vitro transcription assays with Tat were performed as described previously (Madore et al., Song et al., Suen et al.) with modifications. 100 ng of supercoiled pHIV-1-LTR template was used in each reaction (25 μl). The reactions were further incubated for 30 minutes and then stopped with the addition of 1 μl of RNAseT1 5 U /μl) and incubated at 37° C. for 10 minutes.

First, the level of TIP1 in the HeLa nuclear extract was compared with the levels in mock-depleted and TIP1-depleted extracts by Western blot analysis with anti-TIP. As revealed in FIG. 7A, approximately 90% of TIP1 was removed from the extracts by passage through the anti-TIP1 column.

Next, the substantial removal of TIP1 from nuclear extract was tested to determine whether such removal would affect either basal transcription or activated transcription mediated by DNA-binding transcriptional activators such as Gal-VP16 (18) and Gal-Sp1. Mock-depleted and anti-TIP1-depleted nuclear extracts were assayed for transcription from both the core adenovirus major late promoter and a promoter containing the HIV TATA box and five Gal4 binding site upstream TATA box. As shown in FIG. 7B, there were no significant effects of TIP1 depletion on either basal transcription or on activated transcription by Gal-VP16 and Gal-Sp1. This result suggests that TIP1 is neither a general basal factor nor a general cofactor. This is consistent with the finding from transient transfection assays that TIP1 does not stimulate transactivation by DNA-binding activators Gal-VP16, Gal-p53 and Gal-E1A (FIG. 7B). Then, testing was done to determine whether TIP1 is required for transactivation of the HIV-1 promoter by Tat. As demonstrated in FIG. 7C, no significant effect on Tat-independent transcription of the HIV1 promoter was observed in TIP1-depleted extract (compare lane 1 with lane 3). In striking contrast, the TIP1 depleted extract failed to support Tat-dependent transcription (FIG. 7C, compare lanes 2 and 4). When added to the TIP1-depleted nuclear extract, the endogenous TIP1 purified from HeLa nuclear extract (fraction 32 from the gel filtration column in FIG. 4) fully restored Tat activated transcription while bacterially-expressed recombinant TIP1 partially restored this activity (FIG. 7D). In contrast, neither the natural TIP1 nor the recombinant TIP1 affected Tat-independent transcription of the HIV1 promoter (FIG. 7D). This result indicates that among the activators tested, TIP1 is required specifically for transactivation by Tat. The observation that recombinant TIP1 is less active than the natural TIP1 indicates that full activities of TIP1 may require either post-translational modification of TIP1 or an associated regulatory factor that could be partially depleted by anti-TIP1 antibodies.

Genetic and biochemical studies have suggested that at least two cellular cofactors are required for transactivation by Tat in human cells: one that binds to the loop of TAR and facilitates binding of Tat to TAR and another that interacts with the amino-terminal portion of Tat. Although several cellular proteins have been found to interact with TAR RNA in vitro, only the 185 kDa protein, termed TRP-185, appears to be a prominent candidate for the primary TAR-binding cofactor. Binding of TRP-185 to TAR is dependent on the loop sequences of TAR and on TRP-185-associated factors. The latter is reported to consist of elongation factor 1α (EF-1α), the polypyrimidine tract-binding protein, and a novel protein designated the stimulator of TAR RNA-binding protein. Therefore, TRP-185 and its associated factors may represent the TAR loop-binding cofactor of Tat.

Evidence for the existence of a Tat-interacting cofactor activity in human cells first emerged from studies demonstrating that Tat mutants lacking the basic domain were able to inhibit transactivation by Tat. Indirect studies have also suggested that this cofactor activity can interact with the activation domain of HIV-1 Tat, but not the activation domain of the herpes simplex virus protein VP16. Candidates for Tat interacting cofactors have also been reported (Madore et al., *J. Virol.* 67, 3703 (1993); Song et al., *Proc. Natl. Acad. Sci.* USA 91, 9357 (1994)) and include TBP1, MSS1, TAP, and Tip60. Although these proteins have some of the expected characteristics of a Tat cofactor, none have been determined to directly participate in the action of Tat as cofactors. More recent studies using cell-free transcription assays have reported the partial purification of a novel Tat cofactor called Tat-SF. One component (Tat-SF1) of Tat-SF was identified as a 140 kDa phosphorylated protein and a cognate cDNA encoding Tat-SF1 for Tat-dependent transcription was indicated by combined immunodepletion and in vitro transcription assays and by cotransfection assays. Since the in vitro immunodepletion assays were not performed with nuclear extract, it is not clear that Tat-SF1 is essential for Tat-activated transcription. In addition, coexpression of SF1 and Tat did not increase Tat activated transcription in vivo. Rather, Tat relieved an inhibition of transcription that was caused by overexpression of Tat-SF1.

TIP1 shares no significant homology with any of these proteins, suggesting that it is a novel Tat coactivator. The present data demonstrates that TIP1 is required specifically for Tat-activated transcription in vitro. Furthermore, unlike Tat-SF1, overexpression of TIP1 potentiates transactivation by Tat in vivo. Therefore, it is likely that TIP1 plays a role that is distinct from that of Tat-SF1 in mediating transactivation by Tat.

Although the exact mechanism by which TIP1 stimulates transactivation by Tat is not known, it is clear that TIP1 binds to the activation domain of Tat. It has also been observed that TIP1 is present in an RNA polymerase II holoenzyme complex (H. Pan and J. Greenblatt, unpublished data) that was purified by TFIIS affinity chromatography (data not shown). Therefore, Tat may associate with RNA polymerase II holoenzyme complex via interaction with TIP1. Since previous studies suggest that TAT may increase transcription through interaction with transcription factor TFIIH and enhancement of its RNA polymerase II CTD kinase activity, it is possible that interaction between Tat and TIP1 also may regulate phosphorylation of RNA polymerase II or of another component involved in elongation. Although autophosphorylation of TIP1 was not demonstrated, phosphorylation of RNA polymerase II, TBP, TFIIF, and TFIIE by recombinant TIP1 might have other substrates or be dependent upon interactions in an initiation or elongation complex for kinase functions. Indeed, the similarity in amino acid sequences between TIP1 and a protein kinase indicate that TIP1 is likely to be a kinase that is involved in Tat-activated transcription.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

The following is a list of documents related to the above disclosure and particularly to the experimental procedures and discussions. The documents should be considered as incorporated by reference in their entirety.

Jones et al., *Annu. Rev. Biochem.* 63, 717 (1994)

Cullen, *Infect. Agents Dis.* 3, 68 (1994)

Gaynor, Curr. *Top. Microbiol. Immunol.* 193, 51(1989)

Karn et al., *Trends Genet.* 8, 365 (1992).

Feng et al., *Nature* 334, 165 (1988)

Garcia et al., *EMBO J.* 8, 765 (1989)

Selby et al., *Genes Dev.* 3, 547 (1989).

Southgate et al., *Genes Dev.* 5, 2496 (1991).

Sune et al., *J. Virol.* 69, 3098 (1995).

Zhou et al., *Science* 274, 605 (1996).

Cuject et al., *Mol. Cell. Biol.* 17, 1817 (1997).

Gross et al., *J. Biol. Chem.* 265, 6896 (1990).

Emili et al., *Mol. Cell. Biol.* 14, 1582 (1994).

Wu et al., *Genes and Dev.* 5, 2128 (1991).

Wu-Baer et al., *J. Biol. Chem.* 271, 4201 (1996).

Nelbock et al., *Science* 248, 1650 (1990)

Shibuya et al., *Nature* 357, 700 (1992)

Yu et al., *J. Virol.* 69, 3007 (1995)

Kamine et al., *Virology* 216, 357 (1996);

Fridell et al., *Virology* 209, 347 (1995).

Zhou et al., *EMBO J* 14, 321 (1995).

Parada et al., *Nature* 384, 375 (1996).

Rosen et al., *Cell* 41, 813 (1985).

What is claimed is:

1. An isolated DNA molecule comprising a DNA sequence of SEQ ID NO:3, or a fragment thereof comprising 15–25 base pairs.

2. An isolated DNA molecule hybridizable to the isolated DNA molecule of claim 1 under hybridization conditions of 5×SSC and 65° C.

3. An isolated DNA molecule which encodes a Tat-interacting protein 30 (TIP30) comprising an amino acid sequence of SEQ ID NO:1.

4. The isolated DNA molecule of claim 3, comprising a DNA sequence of SEQ ID NO:3.

5. An expression vector comprising the isolated DNA molecule of any of claims 1, 2 or 3, operatively linked to an expression control sequence.

6. The expression vector of claim 5, wherein said expression control sequence comprises an early promoter of SV40, a late promoter of SV40, an early promoter of adenovirus, a late promoter of adenovirus, the lac system, the trp system, the TAC system, the TRC system, the major operator and promoter regions of phage λ, the control regions of fd coat protein, the promoter for 3-phosphoglycerate kinase, a promoter of acid phosphatase, or a promoter of yeast a-mating factor.

7. The expression vector of claim 5, comprising plasmid pGEX-3X clone E3, or plasmid pGEX-3X, clone E4.

8. A unicellular host transformed with the expression vector of claim 5.

9. The unicellular host of claim 8, comprising E. coli, Pseudomonas, Bacillus, Streptomyces, yeasts, CHO, R1.1, B-W, L-M, COS 1, COS 7, BSC1, BSC40, BMT10, a plant cell, an insect cell, or a human cell in tissue culture.

10. An isolated DNA molecule comprising a DNA sequence of SEQ ID NO:4, or a fragment thereof comprising 15–25 base pairs.

11. An isolated DNA molecule hybridizable to the isolated DNA molecule of claim 10 under hybridization conditions of 5×SSC and 65° C.

12. An isolated DNA molecule which encodes a Tat-interacting protein 30 (TIP30) comprising an amino acid sequence of SEQ ID NO:2.

13. The isolated DNA molecule of claim 11, comprising a DNA sequence of SEQ ID NO:4.

14. An expression vector comprising the isolated DNA molecule of any of claims 10, 11, or 12 operatively linked to an expression control sequence.

15. The expression vector of claim 14, wherein said expression control sequence comprises an early promoter of SV40, a promoter of SV40, an early promoter of adenovirus, a late promoter of adenovirus, the lac system, the trp system, the TAC system, the TRC system, the major operator and promoter regions of phage λ, the control regions of fd coat protein, the promoter for 3-phosphoglycerate kinase, a promoter of acid phosphatase, or a promoter of yeast a-mating factor.

16. A unicellular host transformed with the expression vector of claim 14.

17. The unicellular host of claim 16, comprising E. coli, Pseudomonas, Bacillus, Streptomyces, yeasts, CHO, R1.1, B-W, L-M, COS 1, COS 7, BSC1, BSC40, BMT10, a plant cell, an insect cell, or a human cell in tissue culture.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 242 amino acids
       (B) TYPE: amino acid
       (C) STRANDEDNESS: single
       (D) TOPOLOGY: linear (ii) MOLECULE TYPE: protein (iii) HYPOTHETICAL: NO (vi) ORIGINAL SOURCE:
       (A) ORGANISM: Homo sapiens (TIP1)

(xi) SEQUENCE DESCRIPTION: SEQ ID NO:1:

```
Met Ala Glu Thr Glu Ala Leu Ser Lys Leu Arg Glu Asp Phe Arg Met
1               5                   10                  15

Gln Asn Lys Ser Val Phe Ile Leu Gly Ala Ser Gly Glu Thr Gly Arg
            20                  25                  30

Val Leu Leu Lys Glu Ile Leu Glu Gln Gly Leu Phe Ser Lys Val Thr
        35                  40                  45

Leu Ile Gly Arg Arg Lys Leu Thr Phe Asp Glu Glu Ala Tyr Lys Asn
    50                  55                  60

Val Asn Gln Glu Val Val Asp Phe Glu Lys Leu Asp Asp Tyr Ala Ser
65                  70                  75                  80

Ala Phe Gln Gly His Asp Val Gly Phe Cys Cys Leu Gly Thr Thr Arg
                85                  90                  95

Gly Lys Ala Gly Ala Glu Gly Phe Val Arg Val Asp Arg Asp Tyr Val
            100                 105                 110

Leu Lys Ser Ala Glu Leu Ala Lys Ala Gly Cys Lys His Phe Asn
        115                 120                 125

Leu Leu Ser Ser Lys Gly Ala Asp Lys Ser Ser Asn Phe Leu Tyr Leu
    130                 135                 140

Gln Val Lys Gly Glu Val Glu Ala Lys Val Glu Glu Leu Lys Phe Asp
145                 150                 155                 160

Arg Tyr Ser Val Phe Arg Pro Gly Val Leu Leu Cys Asp Arg Gln Glu
                165                 170                 175

Ser Arg Pro Gly Glu Arg Leu Val Arg Lys Phe Phe Gly Ser Leu Pro
            180                 185                 190

Asp Ser Trp Ala Ser Gly His Ser Val Pro Val Thr Val Val Arg
        195                 200                 205

Ala Met Leu Asn Asn Val Val Arg Pro Arg Asp Lys Gln Met Glu Leu
    210                 215                 220

Leu Glu Asn Lys Ala Ile His Asp Leu Gly Lys Ala His Gly Ser Leu
225                 230                 235                 240

Lys Pro
```

(2) INFORMATION FOR SEQ ID NO:2:

(i) SEQUENCE CHARACTERISTICS:
       (A) LENGTH: 242 amino acids
       (B) TYPE: amino acid
       (C) STRANDEDNESS: single
       (D) TOPOLOGY: linear (ii) MOLECULE TYPE: protein (iii) HYPOTHETICAL: NO (vi) ORIGINAL SOURCE:
          (A) ORGANISM: Mus musculus (TIP1)

(xi) SEQUENCE DESCRIPTION: SEQ ID NO:2:

Met Ala Asp Lys Glu Ala Leu Arg Lys Leu Arg Glu Asp Phe Lys Met
1               5                   10                  15

Gln Asn Lys Ser Val Phe Ile Leu Gly Ala Ser Gly Glu Thr Gly Lys
            20                  25                  30

Val Leu Leu Lys Glu Ile Val Gly Gln Asn Leu Phe Ser Lys Val Thr
        35                  40                  45

Leu Ile Gly Arg Arg Lys Leu Thr Phe Glu Glu Glu Ala Tyr Lys Asn
50                  55                  60

Val Asn Gln Glu Val Val Asp Phe Glu Lys Leu Asp Val Tyr Ala Ser
65                  70                  75                  80

Ala Phe Gln Gly His Asp Val Gly Phe Cys Cys Leu Gly Thr Thr Arg
                85                  90                  95

Ser Lys Ala Gly Ala Glu Gly Phe Val Arg Val Asp Arg Asp Tyr Val
            100                 105                 110

Leu Lys Ser Ala Glu Leu Ala Lys Ala Gly Gly Cys Lys His Phe Asn
        115                 120                 125

Leu Leu Ser Ser Arg Gly Ala Asp Lys Ser Ser Ser Phe Leu Tyr Leu
    130                 135                 140

Gln Val Lys Gly Glu Val Glu Ala Lys Val Glu Glu Leu Lys Phe Asp
145                 150                 155                 160

Arg Leu Ser Val Phe Arg Pro Gly Val Leu Leu Cys Asp Arg Gln Glu
                165                 170                 175

Ser Arg Pro Gly Glu Trp Leu Ala Arg Lys Phe Phe Gly Ser Leu Pro
            180                 185                 190

Asp Ser Trp Ala Ser Gly Tyr Ala Val Pro Val Val Thr Val Val Arg
        195                 200                 205

Ala Met Leu Asn Ser Leu Val Ser Pro Ser Ser Gly Gln Met Glu Leu
    210                 215                 220

Leu Glu Asn Lys Ala Ile Leu His Leu Gly Lys Asp Arg Asp Val Pro
225                 230                 235                 240

Lys Leu (2) INFORMATION FOR SEQ ID NO:3:

(i) SEQUENCE CHARACTERISTICS:
          (A) LENGTH: 1315 base pairs
          (B) TYPE: nucleic acid
          (C) STRANDEDNESS: double
          (D) TOPOLOGY: linear (ii) MOLECULE TYPE: cDNA (iii) HYPOTHETICAL: NO (vi) ORIGINAL SOURCE:
          (A) ORGANISM: Homo sapiens (TIP1)

(xi) SEQUENCE DESCRIPTION: SEQ ID NO:3:

GTCTGGCCAG ACATGGCCGA AACAGAAGCC CTGTCGAAGC TTCGGAAGA CTTCAGGATG      60

CAGAATAAAT CCGTCTTTAT TTTGGGCGCC AGCGGAGAAA CCGGCAGAGT GCTCTTAAAG    120

GAAATCCTGG AGCAGGGCCT GTTTTCCAAA GTCACGCTCA TTGGCCGGAG GAAGCTCACC    180

```
TTCGACGAGG AAGCTTATAA AAATGTGAAT CAAGAAGTGG TGGACTTTGA AAAGTTGGAT      240

GACTACGCCT CTGCCTTTCA AGGTCATGAT GTAGGATTCT GTTGCCTGGG TACCACCAGA      300

GGGAAAGCTG GGGCGGAGGG ATTTGTTCGT GTTGACCGAG ATTATGTGCT GAAGTCTGCA      360

GAGCTGGGCA AAACTGGAGG GTGCAAACAT TTCAACTTGC TATCCTCTAA AGGAGCTGAT      420

AAATCAAGCA ATTTTTTATA TCTACAAGTT AAGGGAGAAG TAGAAGCCAA GGTTGAAGAA      480

TTAAAATTTG ATCGTTACTC TGTATTTAGG CCTGGAGTTC TGTTATGTGA TAGGCAAGAA      540

TCTCGCCCAG GTGAACGGCT GGTTAGAAAG TTCTTTGGCT CCTTACCAGA CTCTTGGGCC      600

AGTGGGCATT CTGTGCCTGT GGTGACCGTG GTTAGAGCAA TGCTGAACAA TGTGGTGAGA      660

CCAAGAGACA AGCAGATGGA ACTGCTGGAG AACAAGGCCA TCCATGACCT GGGGAAAGCG      720

CATGGCTCTC TCAAGCCATG ACCACATTGG AGAAATGGTT TTTATTGTCA ACCTTAACAC      780

CCATCACCAA ATCGGTAATT TCAGGGTCTA AAAAAAGTCA GCATGTTTTA ACTTTGTTGT      840

TTTACTATCC TCAGGATCCA TTCCAATCAA GAAATGATGG CTCTGGGTCA GTGGTTCAGA      900

GCCTGGTTAT ACATATAGAT CACTCAGGGA GCTTCCCCCA AATAAAGATT TGTCACCCTA      960

TCTCAAACAA GAATCAAAAT TTCTGGGGCA CAATAATCTG TAATTTTCTT GTTTATACTT     1020

CCCCTGATGC CACTGGTTCC GATGCACTGG CTGGGGGGCC TGCTTTGAAA TGCTTGTCTG     1080

CAGAGTCACA GCAGCCATGA AAACCTTATG ACCGTGCAAA TGATCTGCTC TAAAATTGTT     1140

GACATTCATG TCTCTGAGTT ACAAAAGTGC TAATTCACTA CATGTAATTG TGTAAGTAAA     1200

CATTGTGCCT TTACTACTTC TTTATGTAAT AGAAGTTATA TCCTAAGCTT ATATAATACA     1260

TGGGGAGGAT TAAATAAAGG AATAAAGATG AATGGACAAA AAAAAAAAAA AAAAA          1315
```

(2) INFORMATION FOR SEQ ID NO:4:

(i) SEQUENCE CHARACTERISTICS:
        (A) LENGTH: 1178 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Mus musculus (TIP1)

(xi) SEQUENCE DESCRIPTION: SEQ ID NO:4:

```
AAGCAGGACC ATGATACCCC AAGTTGGAAA TTAACCCTTC ATTAAAGGGA ACAAAAAGTT       60

GGTACCGGCC CCCCCCTCGA GCGCCGCCGG GCAGGTGATT TTTTTTGCCC AACATTAACA      120

ACCCTTTCCC CCAGGGTAAA GAGTGTCACT AGCATTTTGA GACAGGACCC ACGGGTGTTG      180

TTTCCCCCAG CATGGCGGAC AAGGAAGCAC TGCGGAAGCT TCGGGAAGAT TTCAAGATGC      240

AGAATAAATC CGTCTTTATT TTGGGCGCCA GCGGGGAAAC TGGCAAAGTA CTTTTAAAGG      300

AAATCGTGGG ACAGAACCTG TTTTCCAAAG TAACGCTCAT TGGTCGGAGG AAGCTCACCT      360

TCGAGGAGGA AGCTTATAAA AATGTGAATC AAGAAGTGGT GGACTTTGAG AAGCTGGATG      420

TCTATGCTTC TGCCTTTCAA GGTCATGATG TTGGATTCTG TTGCCTGGGC ACCACCAGAA      480

GCAAGGCTGG AGCGGAAGGG TTTGTTCGTG TTGACCGAGA TTATGTGCTC AAGTCTGCAG      540

AGCTGGCGAA AGCAGGAGGG TGCAAACATT TCAACTTGCT GTCCTCCAGG GGGCCGATA      600

AGTCCAGCAG TTTCTTATAC CTACAAGTAA AGGGAGAAGT GGAAGCCAAG GTTGAAGAAT      660

TAAAGTTTGA TCGACTCTCA GTGTTTCGGC CAGGAGTCCT ACTGTGTGAC AGGCAAGAGT      720
```

```
CTCGTCCAGG CGAATGGCTG GCTAGGAAAT TCTTCGGCTC TCTGCCAGAC TCTTGGGCCA      780

GTGGGTACGC TGTGCCTGTG GTGACGGTGG TTAGAGCGAT GCTGAACAGC CTGGTGAGTC      840

CCAGCAGCGG ACAAATGGAA CTTCTGGAAA ATAAGGCCAT CCTCCACCTG GGGAAAGACA      900

GGGATGTGCC CAAACTGTGA CCATGCTGGA GGACATTCGT GAAAACCTCA GTGCCTGTCA      960

CCAAATCAGT CATTTGGGGG CTCTATAAAA AGTCTCTTTG TGGTCCTTTG TGGTGTGCTT     1020

CTCCTTAGCC AAGCGGCTCC ATCAGAAAAT GGCACTACTC CACGTCAGTT GTTGAGAGCC     1080

CCGTTGCTCA TGTAATCATC CAGGCAGCTT TTGGAGAACA GGTTTATATC ATAGACTTAT     1140

ACTTTGTAGG TTGCAAACAG GGATCTCTGG AGGTCACG                             1178
```

(2) INFORMATION FOR SEQ ID NO:5:

(i) SEQUENCE CHARACTERISTICS:
        (A) LENGTH: 226 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: E. coli (xi) SEQUENCE DESCRIPTION: SEQ ID NO:5:

```
Met Ser Arg Gly Ala Gln Gly Arg Gln Phe Cys Lys Gly Ala Lys Met
 1               5                  10                  15

Ser Gln Val Leu Ile Thr Gly Ala Thr Gly Leu Val Gly Gly His Leu
                20                  25                  30

Leu Arg Met Leu Ile Asn Glu Pro Lys Val Asn Ala Ile Ala Ala Pro
            35                  40                  45

Thr Arg Arg Pro Leu Gly Asp Met Pro Gly Val Phe Asn Pro His Asp
50                  55                  60

Pro Gln Leu Ser Asp Ala Leu Ala Gln Val Thr Asp Pro Ile Asp Ile
65                  70                  75                  80

Val Phe Cys Cys Leu Gly Thr Thr Arg Arg Glu Ala Gly Ser Lys Glu
                85                  90                  95

Ala Phe Ile His Ala Asp Tyr Thr Leu Val Val Asp Thr Ala Leu Thr
            100                 105                 110

Gly Arg Arg Leu Gly Ala Gln His Met Leu Val Val Ser Ala Met Gly
        115                 120                 125

Ala Asn Ala His Ser Pro Phe Phe Tyr Asn Arg Val Lys Gly Glu Met
    130                 135                 140

Glu Glu Ala Leu Ile Ala Gln Asn Trp Pro Lys Leu Thr Ile Ala Arg
145                 150                 155                 160

Pro Ser Met Leu Leu Gly Asp Arg Ser Lys Gln Arg Met Asn Glu Thr
                165                 170                 175

Leu Phe Ala Pro Leu Phe Arg Leu Leu Pro Gly Asn Trp Lys Ser Ile
            180                 185                 190

Asp Ala Arg Asp Val Ala Arg Val Met Leu Ala Glu Ser Met Arg Pro
        195                 200                 205

Glu His Glu Gly Val Thr Ile Leu Ser Ser Ser Glu Leu Arg Lys Arg
    210                 215                 220

Ala Glu
225
```

(2) INFORMATION FOR SEQ ID NO:6:

(i) SEQUENCE CHARACTERISTICS:
        (A) LENGTH: 231 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Saccharomyces cerevisiae (xi) SEQUENCE DESCRIPTION: SEQ ID NO:6:

```
Met Asn Gly Leu Val Leu Gly Ala Thr Gly Leu Cys Gly Gly Gly Phe
  1               5                  10                  15

Leu Arg His Ala Gln Glu Ala Pro Gln Phe Ser Lys Val Tyr Ala Ile
             20                  25                  30

Leu Arg Arg Glu Leu Pro Phe Pro Ala Thr Asp Lys Val Val Ala Ile
         35                  40                  45

Val Glu Arg Asp Asn Ser Lys Trp Ser Gln Leu Ile Thr Asn Glu Met
 50                  55                  60

Asn Pro Gln Val Leu Phe Thr Ala Leu Ala Thr Thr Arg Ala Ala Ala
 65                  70                  75                  80

Gly Gly Leu Asp Lys Gln Tyr Lys Ile Asp His Asp Leu Asn Leu Gln
                 85                  90                  95

Leu Ala Gln Ala Ala Lys Glu Lys Gly Cys Glu Thr Ile Val Leu Val
                100                 105                 110

Ser Ser Ala Gly Ala His Pro Asp Ser Arg Phe Gly Tyr Met Lys Met
            115                 120                 125

Lys Gly Glu Ile Glu Arg Asp Val Ile Ala Leu Asp Phe Lys His Ile
130                 135                 140

Ile Ile Leu Arg Pro Gly Pro Leu Leu Gly Glu Arg Thr Asn Ser Lys
145                 150                 155                 160

Gln Ser Gly Phe Gly Gly Asn Leu Thr Ala Ala Leu Gly Thr Arg Val
                165                 170                 175

Tyr Arg Ser Arg Phe Gln Arg Leu Leu Gly Tyr Pro Val Tyr Gly Asp
            180                 185                 190

Glu Val Gly Lys Val Gly Val His Leu Ala Leu Asn Thr Ser Gly Lys
        195                 200                 205

Asp Lys Val Gln Phe Val Ser Ser Lys Asp Ile Leu Asp Ile Ser Ala
    210                 215                 220

Ser Leu Glu Lys Ile Ala Thr
225                 230
```

(2) INFORMATION FOR SEQ ID NO:7:

(i) SEQUENCE CHARACTERISTICS:
        (A) LENGTH: 218 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Caenorhabditis elegans (xi) SEQUENCE DESCRIPTION: SEQ ID NO:7:

```
Met Ser Ser Ala Phe Val Val Gly Ala Thr Gly Ala Val Gly Ser Glu
1               5                   10                  15

Leu Val Lys Leu Leu Ala Glu Ser Thr Lys Phe Ser Lys Val Val Val
            20                  25                  30

Leu Ala Arg Arg Pro Val Asp Gly Ala Thr Gly Asp Lys Leu Ile Gln
            35                  40                  45

Lys Thr Val Asp Phe Asp Lys Leu Glu Glu Asn Ala Glu Asp Ile Gln
50                  55                  60

Gly Val Asp Val Ala Phe Cys Ala Leu Gly Thr Thr Arg Gly Lys Ser
65                  70                  75                  80

Gly Ala Asp Gly Phe Tyr Lys Val Asp His Asp Tyr Val Met Ser Ala
            85                  90                  95

Ala Lys Met Ala Lys Glu Asn Gly Val Lys Gln Phe Val Leu Val Ser
            100                 105                 110

Ser Val Gly Ala Asp Ala Ser Ser Arg Phe Leu Tyr Pro Lys Thr Lys
            115                 120                 125

Gly Glu Val Glu Lys Glu Ile Gly Glu Leu Asn Phe Glu Lys Phe Val
            130                 135                 140

Ile Met Arg Pro Gly Leu Ile Glu Ala Lys Arg Pro Glu Phe Arg Ile
145                 150                 155                 160

Gly Glu Phe Leu Gly Lys Ile Val Thr Ala Pro Leu Gly Leu Phe Ser
            165                 170                 175

Asn Arg Phe Ser Ser Ser Ala Thr Ala Ile Ala Gln Ala Met Ile Asn
            180                 185                 190

Ala Thr Gln Thr Glu Glu Thr Gly Asn Gln Ile Trp Asn Asn Ser Lys
            195                 200                 205

Ile Val Glu Glu Ser Lys Lys Tyr Thr Ala
210                 215
```

(2) INFORMATION FOR SEQ ID NO:8:

(i) SEQUENCE CHARACTERISTICS:
        (A) LENGTH: 272 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:8:

```
Ser Leu Lys Glu Phe Leu Asp Lys Ala Arg Glu Asp Phe Lys Gln Arg
1               5                   10                  15

Trp Glu Asn Pro Ala Gln Asn Thr Ala Cys Leu Asp Asp Phe Asp Arg
            20                  25                  30

Ile Lys Thr Leu Gly Thr Gly Ser Phe Gly Arg Val Met Leu Val Lys
            35                  40                  45

His Lys Gln Ser Gly Asn Tyr Tyr Ala Met Lys Ile Leu Asp Lys Gln
50                  55                  60

Lys Val Val Lys Leu Lys Gln Val Glu His Thr Leu Asn Glu Lys Arg
65                  70                  75                  80

Ile Leu Gln Ala Ile Asp Phe Pro Phe Leu Val Asn Met Thr Phe Ser
            85                  90                  95

Leu Lys Asp Asn Ser Asn Leu Tyr Met Val Leu Glu Phe Ile Ser Gly
            100                 105                 110

Gly Glu Met Phe Ser His Leu Arg Arg Ile Gly Arg Phe Ser Glu Pro
```

```
                 115                 120                 125
His Ser Arg Phe Tyr Ala Ala Gln Ile Val Leu Ala Phe Glu Tyr Leu
    130                 135                 140

His Ser Leu Asp Leu Ile Tyr Arg Asp Leu Lys Pro Glu Asn Leu Leu
145                 150                 155                 160

Ile Asp Ser Thr Gly Tyr Leu Lys Val Thr Asp Phe Gly Phe Ala Lys
                165                 170                 175

Arg Val Lys Gly Arg Thr Trp Thr Leu Cys Gly Thr Pro Glu Tyr Leu
            180                 185                 190

Ala Pro Glu Ile Ile Leu Ser Lys Gly Tyr Asn Lys Ala Val Asp Trp
        195                 200                 205

Trp Ala Leu Gly Val Leu Ile Tyr Glu Met Ala Ala Gly Tyr Pro Pro
    210                 215                 220

Phe Phe Ala Asp Gln Pro Ile Gln Ile Tyr Glu Lys Ile Val Ser Gly
225                 230                 235                 240

Lys Val Lys Phe Pro Ser His Phe Ser Asn Glu Leu Lys Asp Leu Leu
                245                 250                 255

Lys Asn Leu Leu Gln Val Asp Leu Thr Lys Arg Tyr Gly Asn Leu Lys
            260                 265                 270

(2) INFORMATION FOR SEQ ID NO:9:

(i) SEQUENCE CHARACTERISTICS:
        (A) LENGTH: 240 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:9:

Ala Glu Thr Glu Ala Leu Ser Lys Leu Arg Glu Asp Phe Arg Met Gln
1               5                   10                  15

Asn Lys Ser Val Phe Ile Leu Gly Ala Ser Gly Glu Thr Gly Arg Val
            20                  25                  30

Leu Leu Lys Glu Ile Leu Glu Gln Gly Leu Phe Ser Lys Val Thr Leu
        35                  40                  45

Ile Gly Arg Arg Lys Leu Thr Phe Asp Glu Glu Ala Tyr Lys Asn Val
    50                  55                  60

Asn Gln Glu Val Val Asp Phe Lys Leu Asp Tyr Ala Ser Ala
65                  70                  75                  80

Phe Gln Gly His Asp Val Gly Phe Cys Cys Leu Gly Thr Thr Arg Gly
                85                  90                  95

Lys Ala Gly Ala Glu Gly Phe Val Arg Val Asp Arg Asp Tyr Val Leu
            100                 105                 110

Lys Ser Ala Glu Leu Ala Lys Ala Gly Gly Cys Lys His Phe Asn Leu
        115                 120                 125

Leu Ser Ser Lys Gly Ala Asp Lys Ser Ser Asn Phe Leu Tyr Leu Gln
    130                 135                 140

Val Lys Gly Glu Val Glu Ala Lys Val Glu Glu Leu Lys Phe Asp Arg
145                 150                 155                 160

Tyr Ser Val Phe Arg Pro Gly Val Leu Leu Cys Asp Arg Gln Glu Ser
                165                 170                 175

Arg Pro Gly Glu Arg Leu Val Arg Lys Phe Phe Gly Ser Leu Pro Asp
            180                 185                 190
```

```
-continued

Ser Trp Ala Ser Gly His Ser Val Pro Val Val Thr Val Val Arg Ala
        195                 200                 205

Met Leu Asn Asn Val Val Arg Pro Arg Asp Lys Gln Met Glu Leu Leu
        210                 215                 220

Glu Asn Lys Ala Ile His Asp Leu Gly Lys Ala His Gly Ser Leu Lys
225                 230                 235                 240
```